United States Patent
Huh et al.

(10) Patent No.: US 11,814,613 B2
(45) Date of Patent: Nov. 14, 2023

(54) LUNG DISEASE MODELS ON A CHIP

(71) Applicant: THE TRUSTEES OF THE UNIVERSITY OF PENNSYLVANIA, Philadelphia, PA (US)

(72) Inventors: Dongeun Huh, Villanova, PA (US); Mark Mondrinos, Philadelphia, PA (US); Woo Yul Byun, Richland, WA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 470 days.

(21) Appl. No.: 15/748,039

(22) PCT Filed: Jul. 27, 2016

(86) PCT No.: PCT/US2016/044282
§ 371 (c)(1),
(2) Date: Jan. 26, 2018

(87) PCT Pub. No.: WO2017/019778
PCT Pub. Date: Feb. 2, 2017

(65) Prior Publication Data
US 2018/0216058 A1    Aug. 2, 2018

Related U.S. Application Data

(60) Provisional application No. 62/348,055, filed on Jun. 9, 2016, provisional application No. 62/348,036, filed
(Continued)

(51) Int. Cl.
*C12M 3/00* (2006.01)
*C12M 1/00* (2006.01)
(Continued)

(52) U.S. Cl.
CPC .............. *C12M 21/08* (2013.01); *A61L 27/18* (2013.01); *A61L 27/22* (2013.01);
(Continued)

(58) Field of Classification Search
None
See application file for complete search history.

(56) References Cited

U.S. PATENT DOCUMENTS 9,618,500 B2    4/2017   Giselbrecht et al.
2004/0258571 A1  12/2004  Lee et al.
(Continued)

FOREIGN PATENT DOCUMENTS

| WO | WO 2014/127250 A1 | 8/2014 |
| WO | WO 2015/061907 A1 | 5/2015 |
| WO | WO 2015/138032 A2 | 9/2015 |

OTHER PUBLICATIONS

Li et al. "Macrophages promote benzopyrene-induced tumor transformation of human bronchial epithelial cells by activation of NF-kB and STAT3 signaling in a bionic airway chip culture and in animal models." Oncotarget, vol. 6, No. 11 (Mar. 15, 2015), pp. 8900-8913. (Year: 2015).*
(Continued)

*Primary Examiner* — William H. Beisner
(74) *Attorney, Agent, or Firm* — BakerHostetler

(57) ABSTRACT

The presently disclosed subject matter provides a biomimetic lung disease model, and methods of its production and use. In one exemplary embodiment, the biomimetic lung disease model can include a first and second microchannel with a membrane coated with airway epithelial cells disposed between the microchannels and at least one device coupled to the biomimetic model that delivers an agent to at least one microchannel. In certain embodiments, the agent is cigarette smoke.

19 Claims, 19 Drawing Sheets

US 11,814,613 B2

Page 2

Related U.S. Application Data on Jun. 9, 2016, provisional application No. 62/197,444, filed on Jul. 27, 2015.

(51) Int. Cl.
    C12M 1/12    (2006.01)
    A61L 27/18    (2006.01)
    A61L 27/38    (2006.01)
    A61L 27/52    (2006.01)
    A61L 27/50    (2006.01)
    A61L 27/22    (2006.01)
    A61L 27/36    (2006.01)
    C08L 83/04    (2006.01)
    C12N 5/00    (2006.01)
    G01N 33/50    (2006.01)
    G09B 23/30    (2006.01)
    C12M 3/06    (2006.01)

(52) U.S. Cl.
CPC ....... *A61L 27/3633* (2013.01); *A61L 27/3804* (2013.01); *A61L 27/50* (2013.01); *A61L 27/52* (2013.01); *C08L 83/04* (2013.01); *C12M 3/00* (2013.01); *C12M 23/16* (2013.01); *C12M 23/20* (2013.01); *C12M 25/02* (2013.01); *C12M 25/14* (2013.01); *C12M 29/10* (2013.01); *C12N 5/0018* (2013.01); *C12N 5/0062* (2013.01); *C12N 5/0068* (2013.01); *G01N 33/5005* (2013.01); *G01N 33/5044* (2013.01); *G09B 23/30* (2013.01); *G09B 23/306* (2013.01); *C12N 2533/30* (2013.01); *C12N 2533/54* (2013.01); *C12N 2535/00* (2013.01); *C12N 2537/10* (2013.01)

(56) References Cited

U.S. PATENT DOCUMENTS

| | | |
|---|---|---|
| 2007/0092550 A1 | 4/2007 | Lui |
| 2007/0224677 A1 | 9/2007 | Neumann |
| 2010/0279268 A1 | 11/2010 | Neumann et al. |
| 2011/0250585 A1 | 10/2011 | Ingber et al. |
| 2012/0322097 A1 | 12/2012 | Charest et al. |
| 2013/0309771 A1 | 11/2013 | Gevaert et al. |
| 2013/0344529 A1 | 12/2013 | Giselbrecht et al. |
| 2014/0093905 A1 | 4/2014 | Ingber et al. |
| 2014/0147880 A1 | 5/2014 | Ingber et al. |
| 2014/0158233 A1 | 6/2014 | Leslie et al. |
| 2014/0335496 A1 | 11/2014 | Grego et al. |
| 2014/0342445 A1 | 11/2014 | Ingber et al. |
| 2014/0356849 A1 | 12/2014 | Wikswo et al. |
| 2015/0087004 A1 | 3/2015 | Chen et al. |
| 2015/0104812 A1 | 4/2015 | Grevesse et al. |
| 2015/0329354 A1 | 11/2015 | Kato et al. |
| 2016/0313306 A1* | 10/2016 | Ingber .............. C12M 23/16 |
| 2018/0230415 A1 | 8/2018 | Huh et al. |

OTHER PUBLICATIONS

Rothen-Rutishauser et al. "A Three-Dimensional Cellular Model of the Human Respiratory Tract to Study the Interaction with particles." American Journal of Respiratory Cell and Molecular Biology, vol. 32 (2005), pp. 281-289. (Year: 2005).*
Wang et al. "Live human nasal epithelial cells (hNECs) on chip for in vitro testing of gaseous formaldehyde toxicity via airway delivery," Lab on a Chip, vol. 14 (2014), pp. 677-680. First Published on Nov. 28, 2013. (Year: 2013).*
Choi et al., "A microengineered pathophysiological model of early-stage breast cancer." Lab on a Chip, Jul. 9, 2015, 15, pp. 3350-3357. (Year: 2015).*
Bhatia, et al., "Microfluidic organs-on-chips," Nature Biotechnology, 32(8):760-772 (2014).
Cagnin et al., "Overview of Micro- and Nano-Technology Tools for Stem Cell Applications: Micropatterned and Microelectronic Devices," Sensors, 12:15947-15982 (2012).
De Souza Carvalho et al., "Carrier interactions with the biological barriers of the lung: Advanced in vitro models and challenges for pulmonary drug delivery," Advanced Drug Delivery Reviews, 75:129-140 (2014).
Evans et al., "The role of material structure and mechanical properties in cell-matrix interactions," Journal of Materials Chemistry B, 2:2345-2356 (2014).
Golden et al., "Fabrication of microfluidic hydrogels using molded gelatin as a sacrificial element," Lab on a Chip, 7:720-725 (2007).
U.S. Appl. No. 15/748,066, filed Jan. 26, 2018.
U.S. Appl. No. 15/748,087, filed Jan. 26, 2018.
Huh et al., "Microfabrication of human organs-on-chips," Nature Protocols 8(11):2135-2157 (2013).
Huh et al., "Reconstituting Organ-Level Lung Functions on a Chip," Science, 328:1662-1668 (2010).
International Search Report dated Oct. 21, 2016 in International Application No. PCT/US2016/044321.
International Search Report dated Oct. 5, 2016 in International Application No. PCT/US2016/044313.
International Search Report dated Oct. 7, 2016 in International Application No. PCT/US16/44282.
Jorgensen et al., "Cigarette smoke induces endoplasmic reticulum stress and the unfolded protein response in normal and malignant human lung cells," BMC Cancer 8:229 (2008).
Keisen et al., "Cigarette Smoke Induces an Unfolded Protein Response in the Human Lung: A Proteomic Approach," American Journal of Respiratory Cell and Molecular Biology 38:541-550 (2008).
Kenche et al., "Cigarette smoking affects oxidative protein folding in endoplasmic reticulum by modifying protein disulfide isomerase," FASEB J. 27:965-977 (2013).
Kramann et al., "Perivasculoar Gli1+ Progenitors are Key Contributors to Injury-Induced Organ Fibrosis," Cell Stem Cell 16:51-66 (2015).
Neal et al., "Formation of elongated fascicle-inspired 3D tissues consisting of high-density, aligned cells using sacrificial outer molding," Lab Chip, 14:1907-1916 (2014).
Sakar et al., "Formation and optogenetic control of engineered 3D skeletal muscle bioactuators," Lab Chip, 12:4976-4985 (2012).
Wen et al., "Interplay of matrix stiffness and protein tethering in stem cell differentiation," Nature Materials, 13:979-987 (2014).
Wolz et al., "In vitro genotoxicity assay of sidestream smoke using a human bronchial epithelial cell line," Food and Chemical Toxicology, 40:845-850 (2002).
U.S. Appl. No. 15/748,066, filed May 26, 2020 Response to Non-Final Office Action.
U.S. Appl. No. 15/748,066, filed Feb. 28, 2020 Non-Final Office Action.
U.S. Appl. No. 15/748,066, filed Nov. 20, 2019 Response to Restriction Requirement.
U.S. Appl. No. 15/748,066, filed May 20, 2019 Restriction Requirement.
U.S. Appl. No. 15/748,087, filed Mar. 23, 2020 Response to Non-Final Office Action.
U.S. Appl. No. 15/748,087, filed Sep. 26, 2019 Non-Final Office Action.
U.S. Appl. No. 15/748,087, filed Aug. 26, 2019 Response to Restriction Requirement.
U.S. Appl. No. 15/748,087, filed Feb. 25, 2019 Restriction Requirement.
Klein et al., "An improved 3D tetraculture system mimicking the cellular organisation at the alveolar barrier to study the potential toxic effects of particles on the lung," Particle and Fibre Toxicology 10:31 (2013) available from: https://particleandfibretoxicology.biomedcentral.com/articles/10.1186/1743-8977-10-31.
Amendment and Request for Continued Examination (RCE) received for U.S. Appl. No. 15/748,066, dated Nov. 23, 2020.

(56) References Cited

OTHER PUBLICATIONS

Amendment and Request for Continued Examination (RCE) received for U.S. Appl. No. 15/748,087, dated Dec. 1, 2020.

Annabi, N., et al., "Hydrogel-coated microfluidic channels for cardiomyocyte culture," Lab Chip, vol. 13, May 10, 2013, pp. 3569-3577.

Baker, B.M., et al., "Microfluidics embedded within extracellular matrix to define vascular architectures and pattern diffusive gradients," Lab Chip, Jun. 13, 2013, vol. 13, No. 16, pp. 3246-3252.

Baranski, J.D., et al., "Geometric control of vascular networks to enhance engineered tissue integration and function," PNAS, vol. 110, No. 19, May 7, 2013, pp. 7586-7591.

Bertassoni, L.E., et al., "Hydrogel bioprinted microchannel networks for vascularization of tissue engineering constructs," Lab Chip, vol. 14, No. 13, Jul. 7, 2014, pp. 2202-2211.

Bischel, L.L., et al., "Tubeless microfluidic angiogenesis assay with three-dimensional endothelial-lined microvessels," Biomater., vol. 34, No. 5, Feb. 2013, pp. 1471-1477.

Choi et al., Fabrication of a circular PDMS microchannel for constructing a three-dimensional endothelial cell layer, 36(12), Bioprocess. Biosyst. Eng. (2013).

Esch et al., Characterization of in vitro endothelial linings grown within microfluidic channels, Tiss. Eng. A, 17(23-24):2965-2971 (2011) (Year: 2011).

Final Office Action received for U.S. Appl. No. 15/748,066, dated Aug. 25, 2020.

Final Office Action received for U.S. Appl. No. 15/748,087, dated Jun. 2, 2020.

Hammer, J., et al., A facile method to fabricate hydrogels with microchannel-like porosity for tissue engineering, Tiss. Eng., C, vol. 20, No. 2, Feb. 2014, pp. 169-176.

He, J., et al., "Fabrication of circular microfluidic network in enzymatically-crosslinked gelatin hydrogel" Mater. Sci. Eng. C, vol. 59, Feb. 2016, No. pp 53-60.

Huh, D., et al., "From 3D cell culture to organs-on-chips" Trends Cell Biol., vol. 21, No. 12, Dec. 2011, pp. 745-754.

Issue Fee Payment received for U.S. Appl. No. 15/748,066, dated Apr. 14, 2021.

Jimenez-Torres, J., et al., "LumeNEXT: A Practical Method to Pattern Luminal Structures in ECM Gels" Adv. Healthc. Mater., vol. 5, No. 2, Jan. 2016, pp. 198-204.

Kim, H.J., et al., "Human gut-on-a-chip inhabited by microbial flora that experiences intestinal peristalsis-like motions and flow" Lab Chip, vol. 12, Mar. 18, 2012, pp. 2165-2174.

Liu, J., et al., "Hydrogels for Engineering of Perfusable Vascular Networks" Int. J. Mol. Sci., vol. 16, Jul. 14, 2015, pp. 15997-16016.

Non-Final Office Action received for U.S. Appl. No. 15/748,087, dated Jun. 16, 2021.

Non-Final Office Action received for U.S. Appl. No. 15/748,087, dated Sep. 26, 2019.

Notice of Allowance received for U.S. Appl. No. 15/748,066, dated Jan. 21, 2021.

Park, J., et al., "Real-time measurement of the contractile forces of self-organized cardiomyocytes on hybrid biopolymer microcantilevers," Anal. Chem., vol. 77, No. 20, Oct. 15, 2005, pp. 6571-6580.

Ramadan, O., et al., "In vitro micro-physiological models for translational immunology" Lab Chip, vol. 15, Dec. 2, 2014, pp. 614-636.

Response to Non-Final Office Action received for U.S. Appl. No. 15/748,087, dated Mar. 23, 2020.

Response to Restriction Requirement received for U.S. Appl. No. 15/748,066, dated Nov. 20, 2019.

Restriction Requirement received for U.S. Appl. No. 15/748,066, dated May 20, 2019.

Stokol, T., et al., Little Channels, Big Disease Using Microfluidics to Investigate Cancer Metastasis, Conference ASME 2011 9th International Conference on Nanochannels, Microchannels, and Minichannels, May 11, 2012, pp. 655-661.

Www.merriam-webster.com/dictionary/tissue (accessed Feb. 24, 2020).

Yeon, J.H., et al., "In vitro formation and characterization of a perfusable three-dimensional tubular capillary network in microfluidic devices," Lab Chip, vol. 12, May 24, 2012, pp. 2815-2822.

Yum, K., et al., "Physiologically relevant organs on chips," Biotechnol. J., vol. 9, No. 1, Jan. 2014, pp. 16-27.

* cited by examiner

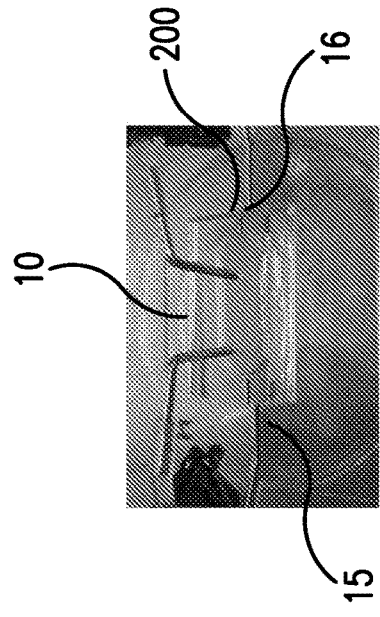
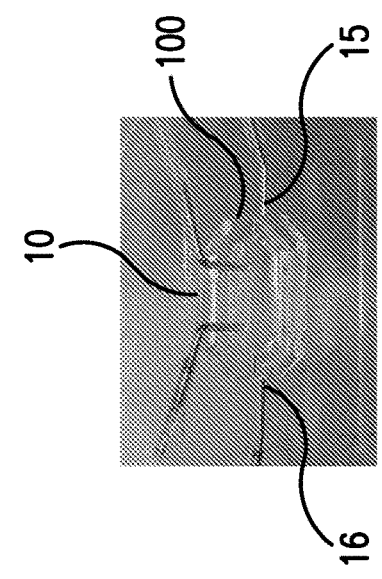
FIG. 1A
FIG. 1B
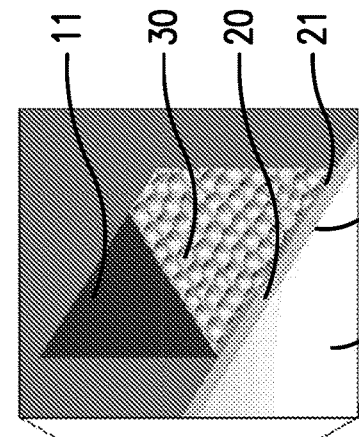
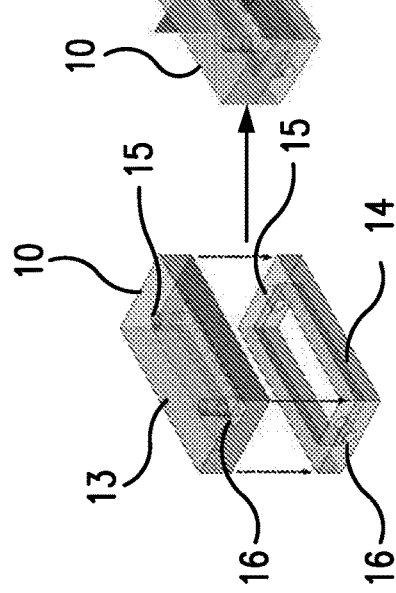
FIG. 2

Increased red staining indicates smoke induced cellular injury

Bronchial epithelial cells
Smoke inlet
4 hours post

Much less red staining when exposed to air only

Bronchial epithelial cells
Air inlet
4 hours post 12 hours after smoke exposure

Smoked

Rounded cell morphology indicative
of dying/apoptotic cells

Air control

Absence of rounded cells

86%

Calcein-AM

93%

Calcein-AM 96.5%

16 hours
(standard)

40 hours 64 hours

LUNG DISEASE MODELS ON A CHIP

CROSS-REFERENCE TO RELATED APPLICATIONS

This application is a U.S. National Phase application under 35 U.S.C. § 371 of International Application No. PCT/US2016/044282, filed on Jul. 27, 2016, which claims priority to U.S. Provisional Application Ser. No. 62/197,444, filed on Jul. 27, 2015, U.S. Provisional Application Ser. No. 62/348,036, filed on Jun. 9, 2016, and U.S. Provisional Application Ser. No. 62/348,055, filed on Jun. 9, 2016, all of which are incorporated by reference herein in their entirety.

BACKGROUND

Toxins and pollutants (e.g. cigarette smoke, silica dust, asbestos fibers, grain dust, and bird and animal droppings) are primary causes of chronic medical conditions and life-threatening malignancies in the lung. Biological underpinnings of these diseases, however, remain poorly understood due to a lack of surrogate models for mechanistic investigation of pathological responses to these toxins and pollutants in a physiological environment.

The structural, functional and environmental complexity of the lung and airways poses certain technical challenges for in vitro investigation of its physiology and pathology using traditional cell culture models. As a result, certain research in this area has relied on expensive and time-consuming ex vivo or in vivo animal studies that can often fail to model biological responses in humans. These drawbacks of existing models can limit the understanding and the development of new therapeutic approaches to lung diseases. Therefore, there is a need for a low-cost, human cell-based alternative to current lung disease models.

One approach to meeting these challenges is to leverage microengineering technologies that provide unprecedented capabilities to control cellular microenvironment with high spatiotemporal precision and to present living cultured cells with external influences and biochemical signals in a more physiologically relevant context. This has led to the development of microengineered biomimetic systems such as "organs-on-chips" that simulate complex organ-level physiology. However, there remains a need for additional physiologically relevant, human cell-based alternatives to model lung disease.

SUMMARY

The presently disclosed subject matter provides a biomimetic lung model and methods of its use. The present disclosure also provides for methods of fabricating the biomimetic lung model. In an exemplary non-limiting embodiment, the biomimetic lung model can include a body, membrane, a layer of cells, and a device coupled to the body that can deliver an agent to the cells. In certain embodiments, the body can have a first and second microchannel. In certain embodiments, the first microchannel can be situated above the second microchannel. In certain embodiments, the membrane can be disposed between the first and second microchannel. In certain embodiments, the membrane can have a first and second side, wherein the first side faces the first microchannel and the second side faces the second microchannel. In certain embodiments, the layer of cells can be disposed on the first side of the membrane. In certain embodiments, the device can deliver an agent to at least one microchannel. In certain embodiments, the device can deliver an agent to one of the first or second microchannels. In certain embodiments, the device can deliver the agent to the first microchannel.

In certain embodiments, the body can have a single microchannel. In certain embodiments, a membrane can be disposed at the bottom of the single microchannel, with a first side facing the interior of the single microchannel and a second side facing the exterior of the body or microchannel. In certain embodiments, the body with a single microchannel and membrane can be placed over a reservoir for feeding.

In certain embodiments, the biomimetic lung model contains most of the major cellular constituents in the airway niches of the human lung. In certain embodiments, the layer of cells comprises airway epithelial cells. In certain embodiments, the airway epithelial cells can comprise Type I and Type II cells. In certain embodiments, the airway epithelial cells can be from all compartments of the lung, including but not limited to, nasal epithelial cells, tracheal epithelial cells, bronchial epithelial cells, small airway epithelial cells and/or alveolar epithelial cells, (e.g., Type I and II cells). In certain embodiments, the platform can model all the different segments/depths of the lung. In certain embodiment, the airway epithelial cells can be from healthy human lung. In certain embodiments, the airway epithelial cells can be from human diseased lung. In certain embodiments, the diseased lung can be chronically diseased. In certain embodiments, the layer of cells can further comprise macrophages. In certain embodiments, the macrophages can be alveolar, interstitial, intravascular, airway macrophages, and/or an immortalized macrophage cell line (e.g., THP-1). In certain embodiments, a layer of vascular endothelial cells can be attached to the second side of the membrane.

In certain embodiments, cells from different parts of the lung can be cultured in separate devices and then linked together in a serial fashion to mimic the entire respiratory tract.

In certain embodiments, a gel layer can be attached to the second side of the membrane. In certain embodiments, the gel can comprise extracellular matrix proteins such as, but not limited to, collagen, fibronectin, laminin, hyaluronic acid, and/or similar materials. In certain embodiments, the gel can comprise collagen. In certain embodiments, tissue or cells can be embedded in the gel. In certain embodiments, the gel layer allows the embedded cells to communicate with the layer of cells on the first side of the membrane. In certain embodiments, the cells embedded in the gel layer can be connective tissue or cells. In certain embodiments, the cells embedded in the gel layer can be basal stromal cells. In certain embodiments, the basal stromal cells can be fibroblasts and/or pericytes. In certain embodiments, the cells embedded in the gel layer can be airway and/or vascular smooth muscle cells. In certain embodiments, the cells embedded in the gel layer can be extracellular matrix proteins. In certain embodiments, the gel contains tethering materials encased within. In certain embodiments, hollow tubes and/or self-assembled living vessel can be created within the gel layer to mimic vascular and lymphatic supply.

In certain embodiments, the membrane can be a porous material that has one or more pores with a width from about 0.4 microns to about 10 microns. In certain embodiments, the pores have a width from about 0.5 microns to about 9 microns, about 0.6 microns to about 8 microns, about 0.7 microns to about 7 microns, about 0.8 microns to about 6 microns, about 0.9 microns to about 5 microns, about 1 microns to about 4 microns, about 1.5 microns to about 3.5 microns, or about 2 microns to about 3 microns. In certain embodiments, the membrane can be one of a thin clear polyester fiber, a polyester membrane, a polytetrafluoroethylene membrane, an elastomeric (e.g., poly(dimethylsiloxane) (PDMS), polyurethane) membrane, a paper membrane, an extracellular matrix membrane, or a natural membrane. In certain embodiments, the natural membrane can be collagen, laminin, or a combination of both.

In certain embodiments, the first microchannel can be above the second microchannel. In certain embodiments, the first microchannel replicates the dimensions of the airways in the native human lung. In certain embodiments, the first microchannel has a width from about 0.1 mm to about 2 mm. In certain embodiments, the first microchannel has a width from about 0.5 mm to about 1 mm.

In certain embodiments, the first microchannel has a width from about 0.5 mm to about 2 mm. In certain embodiments, the first microchannel has a width from about 1 mm to about 2 mm. In certain embodiments, the first microchannel has a width from about 0.6 mm to about 1.9 mm, from about 0.7 mm to about 1.8 mm, from about 0.8 mm to about 1.7 mm, from about 0.9 mm to about 1.6 mm, from about 1 mm to about 1.5 mm, or from about 1.2 mm to about 1.4 mm. In certain embodiments, the first microchannel has a width of at least about 0.5 mm, at least about 0.75 mm, at least about 1 mm, at least about 1.25 mm, at least about 1.5 mm, at least able 1.75 mm, or at least about 2 mm. In certain embodiments, the first microchannel has a width of about 100 µm to about 500 µm. In certain embodiments, the first microchannel has a width of about 100 µm to about 400 µm. In certain embodiments, the first microchannel has a width of about 100 µm to about 300 µm. In certain embodiments, the first microchannel has a width of about 100 µm to about 200 µm. In certain embodiments, the first microchannel has a width of about 110 µm to about 190 µm, about 120 µm to about 180 µm, about 130 µm to about 170 µm, or about 140 µm to about 160 µm. In certain embodiments, the first microchannel has a length from about 1000 µm to about 10 mm. In certain embodiments, the first microchannel has a length from about 1010 µm to about 9 mm, about 1020 µm to about 8 mm, about 1030 µm to about 7 mm, about 1040 µm to about 6 mm, about 1050 µm to about 5 mm, about 1060 µm to about 4 mm, about 1070 µm to about 3 mm, about 1080 µm to about 2 mm, about 1090 µm to about 1900 µm, about 1100 µm to about 1800 µm, about 1200 µm to about 1700 µm, about 1300 µm to about 1600 µm, or about 1400 µm to about 1500 µm. In certain embodiments, the first microchannel has a width from about 1 mm to about 2 mm. In certain embodiments, the first microchannel has a length of about 1000 µm. In certain embodiments, the body includes one or more flow channels. In certain embodiments, the body further includes one or more microfabricated openings or ports. In certain embodiments, the biomimetic lung model optimizes air-liquid interface culture. In certain embodiments, the first microchannel can have air or gases flowing through the microchannel. In certain embodiments, the first microchannel can have culture medium flowing through the microchannel. In certain embodiments, the second microchannel can serve as a reservoir for basal feeding. In certain embodiment, the second microchannel can have culture medium flowing through the microchannel. In certain embodiment, the second microchannel can have cell media held within its reservoir.

In certain embodiments, the device can deliver an agent to the first microchannel. In certain embodiments, the agent can be cigarette smoke, nicotine aerosol, wood smoke, natural plant smoke, silica dust, acrylic dust, particulates, asbestos fibers, solvents, grain dust, bird droppings, and animal droppings. In certain embodiments, the device delivers cigarette smoke to the first microchannel. In certain embodiments, the device delivering the cigarette smoke can be an automatic smoking machine. In certain embodiments, the cigarette smoke can be delivered to the first microchannel such that the distribution of cigarette smoke mimics cigarette smoke exposure conditions experience by cell linings in the human lung. In certain embodiments, the cigarette smoke can be more dilute the deeper it moves into the first microchannel.

The presently disclosed subject matter further provides methods for producing a biomimetic lung model. In certain embodiments, the method can include fabricating a body. In certain embodiments, the body can have first and second microchannel disposed therein. In certain embodiments, the method can include inserting a membrane between the first and second microchannels. In certain embodiments, the membrane can have a first side and a second side. In certain embodiments, the method can include adhering a layer of cells to the first side of the membrane. In certain embodiments, the layer of cells comprise airway epithelial cells. In certain embodiments, the method can include integrating macrophage cells among the airway epithelial cells. In certain embodiments, the method can include coupling at least one device to the body that delivers an agent to at least one microchannel. In certain embodiments, the method can include delivering an agent to the first microchannel. In certain embodiments, the method can include delivering an agent to one of the first or second microchannels. In certain embodiments, the agent can be cigarette smoke. In certain embodiments, the method can include delivering a culture medium through the first and/or second microchannel. In certain embodiments, the method can include delivering a culture medium through the first and/or second microchannel and then exchanging the flow of medium to the flow of air (with or without the agent) through the first microchannel.

In certain embodiments, adhering the layer of cells to the first side of the membrane can include standard approaches of extracellular matrix coating of the membrane, for example, but not limited to the use of fibronectin, prior to seeding of cells. In certain embodiments, to seed the cells, a high density cell suspension can be introduced to the channel and allowed to incubate under static conditions to allow the cells to adhere. In certain embodiments, the cell suspension is allowed to incubate for 2 to 4 hours. In certain embodiments, after the period of attachment flow can be initiated to allow the washing away of unattached cells and beginning the perfused culture stage. In certain embodiments, some cell proliferation can occur to fill out the entire membrane surface. In certain embodiments, cell proliferation is allowed to occur for 2-3 days.

In certain embodiments, the method can include attaching a gel layer to the second side of the membrane. In certain embodiments, the gel can be composed of collagen. In certain embodiments, tissue or cells can be embedded in the gel. In certain embodiments, basal stromal tissue or cells can be embedded in the gel.

In certain embodiments, the method can include casting a gel. Gel casting can involve any standard method known to one of skill in the art. In certain embodiments, techniques are used to induce surface modification to promote collegen/ECM anchoring. In certain embodiments, the casting of a gel can include sulfo-sanpah treatment of the membrane material to promote collagen/ECM anchorage. In certain embodiments, the gel is prepared with cells and pipetted onto the second side of the membrane that has been stamped to a channel. In certain embodiments, the gel is prepared without cells and pipetted onto the second side of the membrane. In certain embodiments, after the gel layer solidifies, the upper channel portion—now with a cast gel under the membrane—can be flipped back over and placed over the reservoir layer to complete the device assembly.

In accordance with certain embodiments of the disclosed subject matter, a method of testing the effects of a toxic agent on the layer of cells. In certain embodiments, the method can include providing a biomimetic lung model, as described hereinabove. In certain embodiments, the method can include placing an agent of interest in one of the first or second microchannels. In certain embodiments, the method can include simulating physiological conditions. In certain embodiments, the method can include measuring pathological responses to the agent. In certain embodiments, the method can include measuring tissue hardening in response to the agent. In certain embodiments, the agent of interest can be cigarette smoke, nicotine aerosol, wood smoke, natural plant smoke, silica dust, acrylic dust, particulates, asbestos fibers, solvents, grain dust, bird droppings, and animal droppings.

In certain embodiments, the biomimetic lung model can be a model of lung inflammatory diseases. For example, the presence of macrophages allows for looking at inflammation. In certain embodiments, the biomimetic lung model can be a model of cigarette smoke-induced airway disease. In certain embodiments, the biomimetic lung model can be a model of smoke-induced emphysema. In certain embodiments, the biomimetic lung model can be a model of chronic obstructive pulmonary disease (COPD). In certain embodiments, the biomimetic lung model can be a model of lung fibrosis. In certain embodiments, the biomimetic lung model can be a model of lung cancer and/or a model to examine premalignant changes in epithelial cells exposed to various agents.

The presently disclosed subject matter further provides methods of using the disclosed biomimetic lung model. In certain embodiments, the biomimetic lung model can be used for identifying pharmaceutical compositions that can treat or prevent lung disease. In certain embodiments, the biomimetic lung model can be used for identifying agents harmful to the lung.

BRIEF DESCRIPTION OF THE FIGURES

FIG. 1A-B. depicts (A) microengineered biomimetic lung model according to certain embodiments (B) microengineered biomimetic lung model according to other certain embodiments.

FIG. 2 depicts a schematic representation of an exemplary model according to the disclosed subject matter.

DETAILED DESCRIPTION

Figure 3:
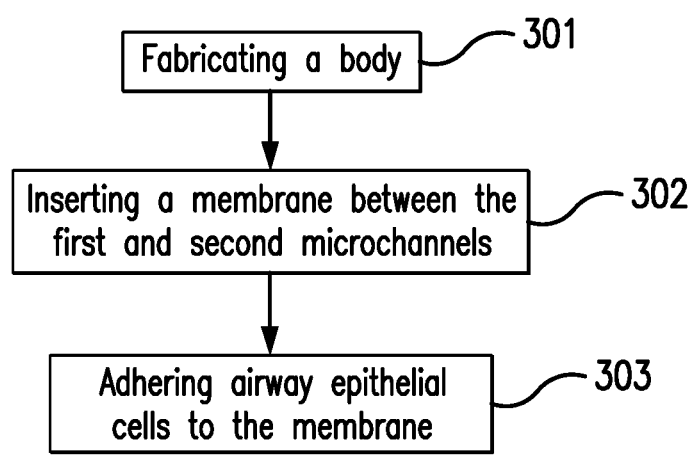
FIG. 3 depicts a schematic representation of an exemplary method according to the disclosed subject matter.

The present disclosure provides a microengineering approach to emulating and probing lung disease processes (e.g., cigarette smoking-induced) in a tissue-engineered microenvironment that recapitulates the complexity of human airways. The disclosed biomimetic lung model can integrate human airway epithelial cells, basal stromal tissue, and airway lumen macrophages with programmable microfluidic delivery of an agent (e.g., cigarette smoke) to study deleterious effects of its exposure on the airway epithelium. The disclosed biomimetic lung model can also utilize human-derived cells to create a microengineered chronic disease model that recapitulated constitutive UPR activation typically observed in chronic obstructive pulmonary disease (COPD).

Biomimetic Lung Model

The presently disclosed subject matter provides a biomimetic lung model. For the purpose of illustration and not limitation, FIG. 1 (A and B) provides exemplary biomimetic lung models 100, 200. In certain embodiments, the biomimetic lung model can include a body 10, a membrane 20, and a layer of cells 30.

In certain embodiments, the base 10 can include a first 11 and second 12 microchannel disposed thereon (FIG. 2). In certain embodiments, the size of the microchannels can replicate the dimensions of the airways in the native human lung. In certain embodiments the microchannels can be about 0.1 mm to about 2 mm wide. In certain embodiments the microchannels can be about 0.1 mm to about 2 mm high. In certain embodiments, the microchannel can be as high as it is wide. In certain embodiments, the height and width of the microchannel can be different. In certain embodiments, the first and second microchannel can have the same dimensions. In certain embodiments, the first and second microchannel can have the different dimensions. In certain embodiments, the microchannels can be each separately about 0.1 mm to about 2 mm wide and about 0.1 mm to about 2 mm high. In certain embodiments, the microchannel can be 1 mm×1 mm. In certain embodiments, the microchannel can be 2 mm×2 mm. In certain embodiments, the microchannel decrease size as the airways in the lung do. For example, one end of the microchannel can be smaller than the other end.

In certain embodiments, one or more of the channels can be about 1000 µm to about 30 mm in length. In certain embodiments, the length is about 1000 µm to about 20 mm. In certain embodiments, the length is about 1000 µm to about 10 mm. In certain embodiments, the length can be about 2 mm to about 25 mm, about 3 mm to about 20 mm about 4 mm to about 15 mm, or about about 5 mm to about 10 mm. In certain embodiments, one or more of the channels can be about 10 mm in length.

In certain embodiments, the base 10 can include additional channels (e.g., four, six, eight, or more, total channels) in pairs of two disposed thereon, with each pair having a membrane disposed therebetween (between the first and second outer body portions 13, 14 when portions 13, 14 are mounted to one another to form the overall body. In certain embodiments, the base 10 can include channels in sets larger than two (e.g., three, four, or more) such that each of the channels in the set can be separated from adjacent channels by a membrane. In certain embodiments, the base 10 can include one or more channels that are not adjacent to another channel, or separated from another channel by a membrane. The number of channels and layouts of the channels, including shape and dimensions, can vary based on the design of the base 10. In certain embodiments, each channel will have generally similar dimensions. In certain embodiments, the channels will have different dimensions. In certain embodiments, the base and microfluidic channels can be made of any suitable material, for example and without limitation, glass, metal, alloy, plastic, wood, paper, and polymer.

In certain embodiments, the membrane 20 can be disposed between the first 11 and second 12 microchannels such that the first 11 and second 12 microchannels can be in fluid communication through the membrane 20. In certain embodiments, the membrane 20 can have a first side 21 and a second side 22. In certain embodiments, the membrane 20 can be a thin clear polyester membrane and can have about 0.4 microns to about 10 microns pores. In certain embodiments, the pores have a diameter from about 0.5 microns to about 9 microns, about 0.6 microns to about 8 microns, about 0.7 microns to about 7 microns, about 0.8 microns to about 6 microns, about 0.9 microns to about 5 microns, about 1 microns to about 4 microns, about 1.5 microns to about 3.5 microns, or about 2 microns to about 3 microns. In certain embodiments, the pores can be any suitable size. In certain embodiments, the pores can have varying pore sizes. In certain embodiments, the thickness of the membrane was about 5 microns to about 100 microns. In certain embodiments, the thickness of the membrane can be about 10 microns to about 90 microns, about 20 microns to about 80 microns, about 30 microns to about 70 microns, about 40 micros to about 60 microns. In certain embodiments, the thickness of the membrane is at least about 5 microns, at least about 10 microns, at least about 20 microns, at least about 30 microns, at least about 40 microns, at least about 50 microns, at least about 60 microns, at least about 70 microns, at least about 80 microns, at least about 90 microns, or at least about 100 microns. In certain embodiments, the membrane can include porous portions and non-porous portions. In certain embodiments, the membrane 20 can be a polyester membrane, a polytetrafluoroethylene membrane, an elastomeric membrane, a paper membrane, an extracellular matrix membrane, a natural membrane or any other suitable membrane. In certain embodiments, the natural membrane may include collagen, laminin, or a combination thereof. The selection of the pore sizes, materials and other features of the membrane can be varied based on the design of the biomimetic lung model, the experimental goals, or other suitable motivations.

In certain embodiments, the layer of cells 30 can be airway epithelial cells. In certain embodiments, the airway epithelial cells can comprise Type I and Type II cells. In certain embodiments, the airway epithelial cells can be from all compartments of the lung, including but not limited to, nasal epithelial cells, tracheal epithelial cells, bronchial epithelial cells, small airway epithelial cells and/or alveolar epithelial cells, (e.g., Type I and II cells). In certain embodiments, the airway epithelial cells are derived from human or animal tissue. In certain embodiments, the airway epithelial cells can be from healthy human or animal lung tissue. In certain embodiments, the airway epithelial cells can be from diseased human or animal lung tissue (e.g., fibrosis, emphysema, COPD, bronchitis, asthma, cystic fibrosis). In certain embodiments, the airway epithelial cells can be differentiated from stem cells (e.g., induced pluripotent stem cells, embryonic stem cells). In certain embodiments, the biomimetic lung model can be a model for smoking-induced emphysema or COPD. In certain embodiments, the smoking-induce emphysema or COPD can involve the pathological structural changes in the lung that take place over years. In certain embodiments, the agent causes oxidative stress.

In certain embodiments, the biomimetic lung model contains most of the major cellular constituents in the airway niches of the human lung. In certain embodiments, the diseased lung can be chronically diseased. In certain embodiments, the layer of cells can further comprise macrophages. In certain embodiments, the macrophages can be alveolar, interstitial, intravascular, airway macrophages and/ or an immortalized cell line (e.g., THP-1). In certain embodiments, the macrophage cells can be added to the cell layer on the first side of the membrane at a ration of about 1 macrophage to about 50 epithelial cells, about 1 macrophage to about 45 epithelial cells, about 1 macrophage to about 40 epithelial cells, about 1 macrophage to about 35 epithelial cells, about 1 macrophage to about 30 epithelial cells, about 1 macrophage to about 25 epithelial cells, about 1 macrophage to about 20 epithelial cells, about 1 macrophage to about 18 epithelial cells, about 1 macrophage to about 16 epithelial cells, about 1 macrophage to about 14 epithelial cells, about 1 macrophage to about 12 epithelial cells, about 1 macrophage to about 10 epithelial cells, about 1 macrophage to about 8 epithelial cells, about 1 macrophage to about 6 epithelial cells, or about 1 macrophage to about 5 epithelial cells.

In certain embodiments, the macrophages are added to the gel layer. In certain embodiments, the macrophages can be added to the gel layer at a ratio of about 1 macrophage to about 8 basal stromal cells, about 1 macrophage to about 7 basal stromal cells, about 1 macrophage to about 6 basal stromal cells, about 1 macrophage to about 5 basal stromal cells, about 1 macrophage to about 4 basal stromal cells, or about 1 macrophage to about 3 basal stromal cells.

In certain embodiments, a second layer of cells 40 can be adhered to the second side of the membrane. In certain embodiments, the second layer of cells can be endothelial cells including pulmonary microvascular endothelial cells. In certain embodiments, the second layer of cells can be large vessel endothelial cells, arterial endohtelial cells, venous endothelial cells all from lung. In certain embodiments, the second layer of cells can be lymphatic endothelial cells. In certain embodiments, the first layer of cells 30 and second layer 40 of cells can be cultured in apposition on a membrane 20. In certain embodiments, the first or second cell layer can have an artificially induced pathology. In certain embodiments, the cell layers can be monolayers.

In certain embodiments, a cell-laden gel layer can be added to the biomimetic model. In certain embodiments, a gel layer can be attached to the second side of the membrane. In certain embodiments, the gel can comprise collagen. In certain embodiments, tissue or cells can be embedded in the gel. In certain embodiments, the gel layer allows the embedded cells to communicate with the layer of cells on the first side of the membrane. In certain embodiments, the cells embedded in the gel layer can be connective tissue or cells. In certain embodiments, the cells embedded in the gel layer can be basal stromal cells. In certain embodiments, the basal stromal cells can be fibroblasts and/or pericytes. In certain embodiments, the cells embedded in the gel layer can be airway and/or vascular smooth muscle cells. In certain embodiments, the cells embedded in the gel layer can be extracellular matrix proteins. In certain embodiments, the extracellular matrix proteins can be, but not limited to, fibronectin, laminin, hyaluronic acid and/or similar materials.

Referring to FIG. 3 for the purpose of illustration and not limitation, there is provided an exemplary method for fabricating a biomimetic lung model (300). In certain embodiments, the method can include fabricating a body (301), the body having first and second microchannels disposed thereon. The body, including the microchannels, can be built by any methods known in the art, including, but not limited to, those outlined in Huh et al., Nature Protocols 8:2135-2157 (2013).

In certain embodiments, the method can include inserting a membrane between the first and second microchannels (302) such that the first and second microchannels can be in fluid communication through the membrane. In certain embodiments, the membrane can have a first and second side. In certain embodiments, the method can include adhere a layer of cells (303) of a first cell type disposed on a first side of the membrane.

Figure 4:
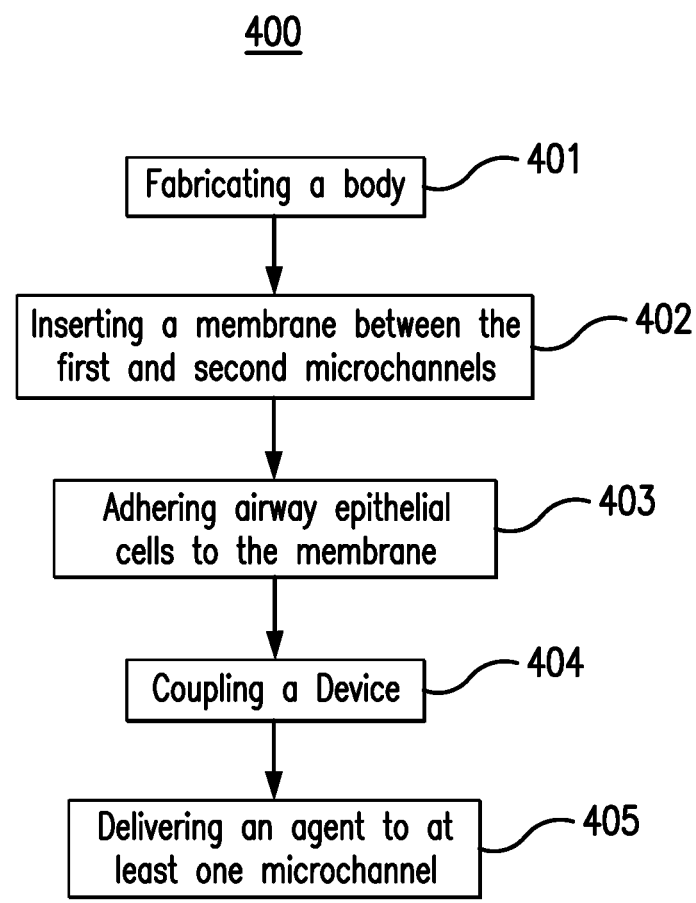
FIG. 4. depicts a schematic representation of an exemplary method according to the disclosed subject matter.

Referring to FIG. 4 for the purpose of illustration and not limitation, there is provided an exemplary method for fabricating a biomimetic lung model (400). In certain embodiments, the biomimetic lung model can be a model of a diseased lung. In certain embodiments, the method can include fabricating a body (401), the body having first and second microchannels disposed thereon. In certain embodiments, the method can include inserting a membrane between the first and second microchannels (402) such that the first and second microchannels can be in fluid communication through the membrane. In certain embodiments, the membrane can have a first and second side. In certain embodiments, the method can include adhering a layer of cells (303) of a first cell type disposed on a first side of the membrane. In certain embodiments, the method can include coupling a device to the body (404). In certain embodiments, the method can include the device delivering an agent to at least one of the microchannels.

In certain embodiments, the method can include casting a gel and attaching a gel to the second side of the membrane. In certain embodiments, the casting of a gel can include sulfo-sanpah treatment of the membrane material to promote collagen/ECM anchorage. In certain embodiments, the gel is prepared with cells and pipetted onto the second side of the membrane that has been stamped to a channel. In certain embodiments, the gel is prepared without cells and pipetted onto the second side of the membrane. In certain embodiments, after the gel layer solidifies, the upper channel portion—now with a cast gel under the membrane—can be flipped back over and placed over the reservoir layer to complete the device assembly.

Figure 5:
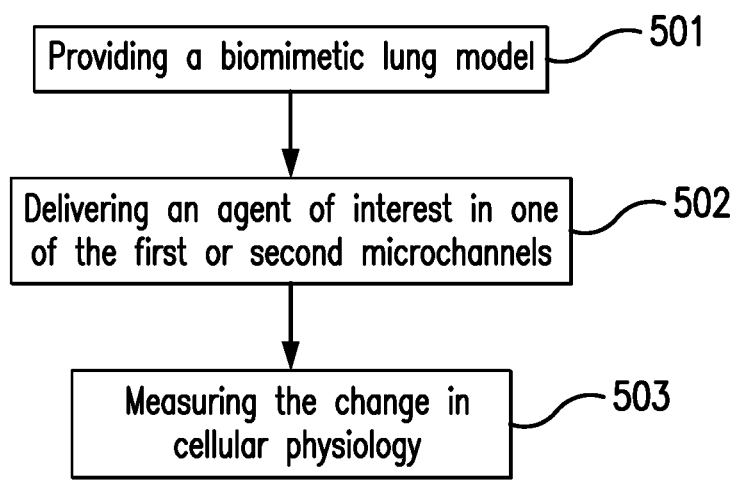
FIG. 5 depicts a schematic representation of an exemplary method according to the disclosed subject matter.

Referring to FIG. 5 for the purpose of illustration and not limitation, an exemplary method of testing metabolic regulation of lung tissue (500) is provided. In certain embodiments, the method can include providing a biomimetic lung model (501) as disclosed herein, and can include delivering an agent of interest in one of the first or second microchannels (502). In certain embodiments, the substance of interest can be, for example, cigarette smoke, nicotine aerosol, automotive exhausts, dry powder drugs, aerosol drugs, ozone, wood smoke, natural plant smoke, silica dust, acrylic dust, particulates, asbestos fibers, solvents, grain dust, bird droppings, and animal droppings. In certain embodiments, the method can include simulating physiological flow conditions. In certain embodiments, the method can include simulating physiological breathing/inhalation conditions. In certain embodiments, the method can include measuring pathological responses to the agent. In certain embodiments, the method can include measuring tissue hardening in response to the agent. In certain embodiments, the method can include measuring inflammatory and other abnormal biological responses, for example, but not limited to, production of cytokines/chemokines & expression of adhesion molecules; activation of oxidative stress pathways, endoplasmic reticulum (protein production) stress; DNA damage; or cell apoptosis and necrosis (death).

Figure 6:
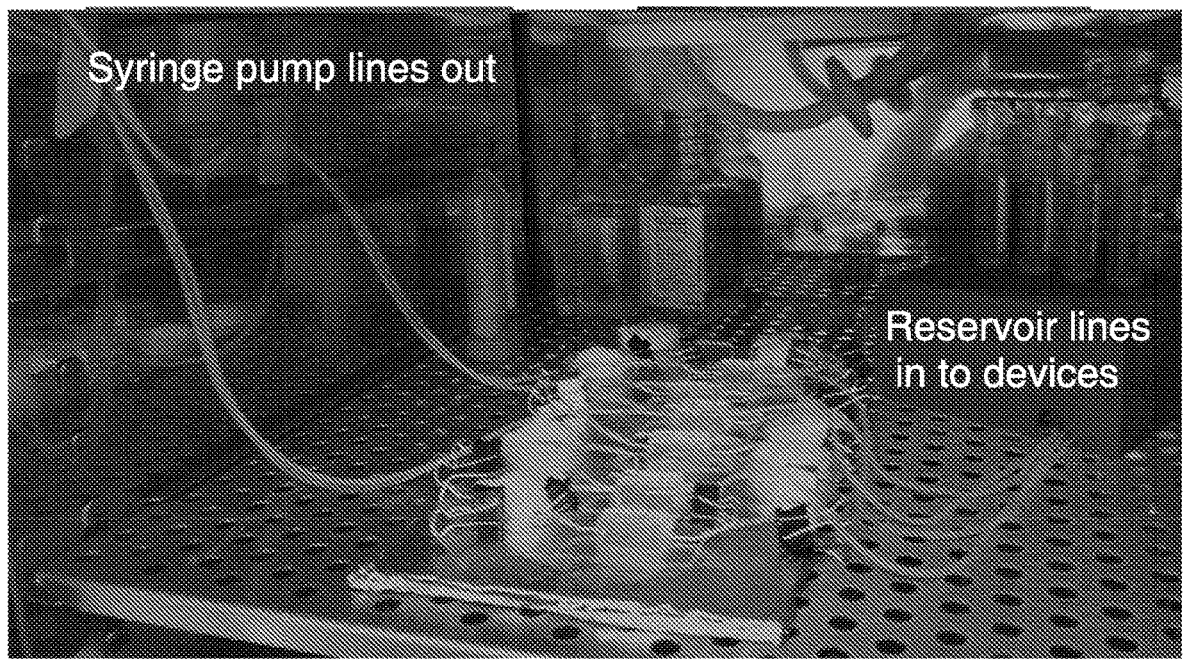
FIG. 6 depicts a microengineered biomimetic lung model according to certain embodiments depicting an exemplary method for delivering culture medium.

In certain embodiments, a device can deliver culture medium to the first and second microchannels (e.g. FIG. 6). In certain embodiments, a device can deliver culture medium to one of the first or second microchannels. In certain embodiments, a device can deliver culture medium to only the second microchannel. In certain embodiments, the device can pump culture medium to the microchannel(s) through a port (e.g., FIGS. 1 and 2 (15)) in the body, wherein the first opening of the port 15 can be to the outside of the body and the second opening of the port 15 can be to at least one microchannel. In certain embodiments, the culture medium leaves the microchannel through an exit port 16. In certain embodiments, the device can pump culture medium out of the microchannel(s) through an exit port 16 in the body, wherein the first opening of the exit port 16 opens to the microchannel and the second opening of the exit port 16 can be to the outside of the body. In certain embodiments the port 15 or exit port 16 only connects to one microchannel. In certain embodiments, the pumping system can draw/pull medium though the channels from a reservoir. In certain embodiments, for the smoke delivery, the smoke can be pulled through the device. In certain embodiments, there can be a mixing chamber in the smoke generation apparatus (i.e., the smoke is generated and diluted/humified in a positive pressure flow process, it then fills an open mixing vessel) from which the smoke/agent mixture can be pulled through the device at a set flow rate via syringe pump. In certain embodiments, the culture medium is not delivered to the biomimetic model while the agent is being delivered. In certain embodiments, the culture medium is delivered to one microchannel while the agent is delivered to the other microchannel.

Figure 7:
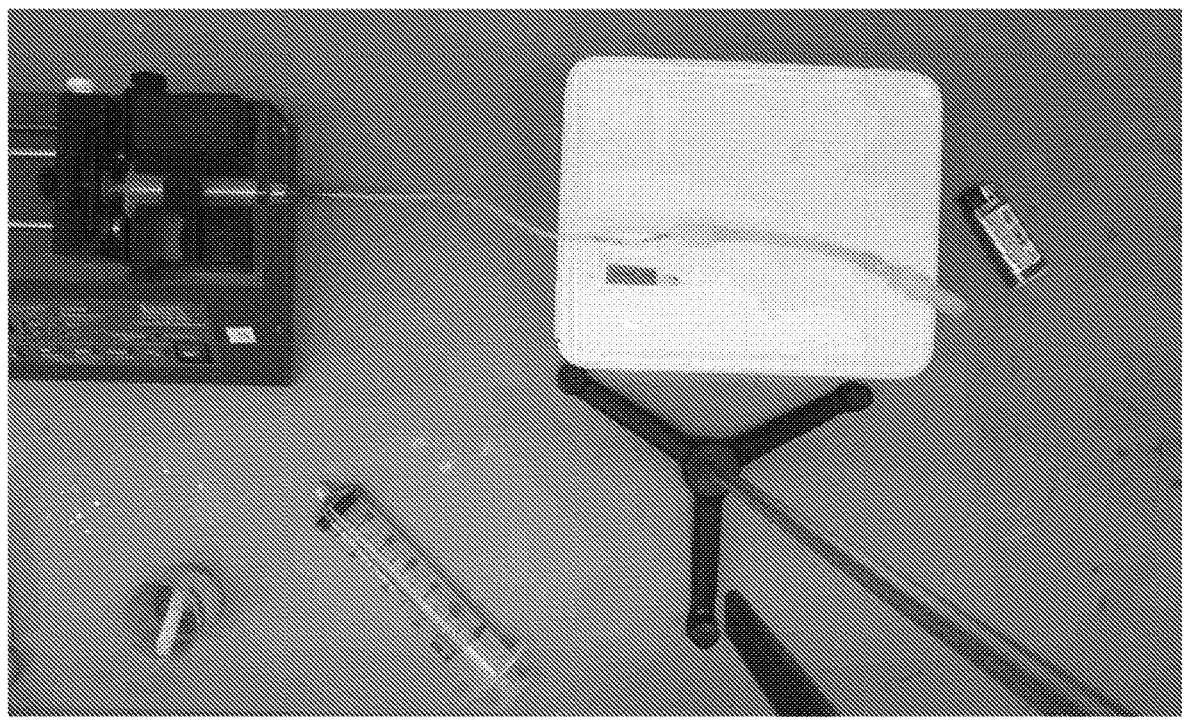
FIG. 7. depicts a microengineered biomimetic lung model according to certain embodiments depicting an exemplary method for delivering cigarette smoke.
Figure 8:
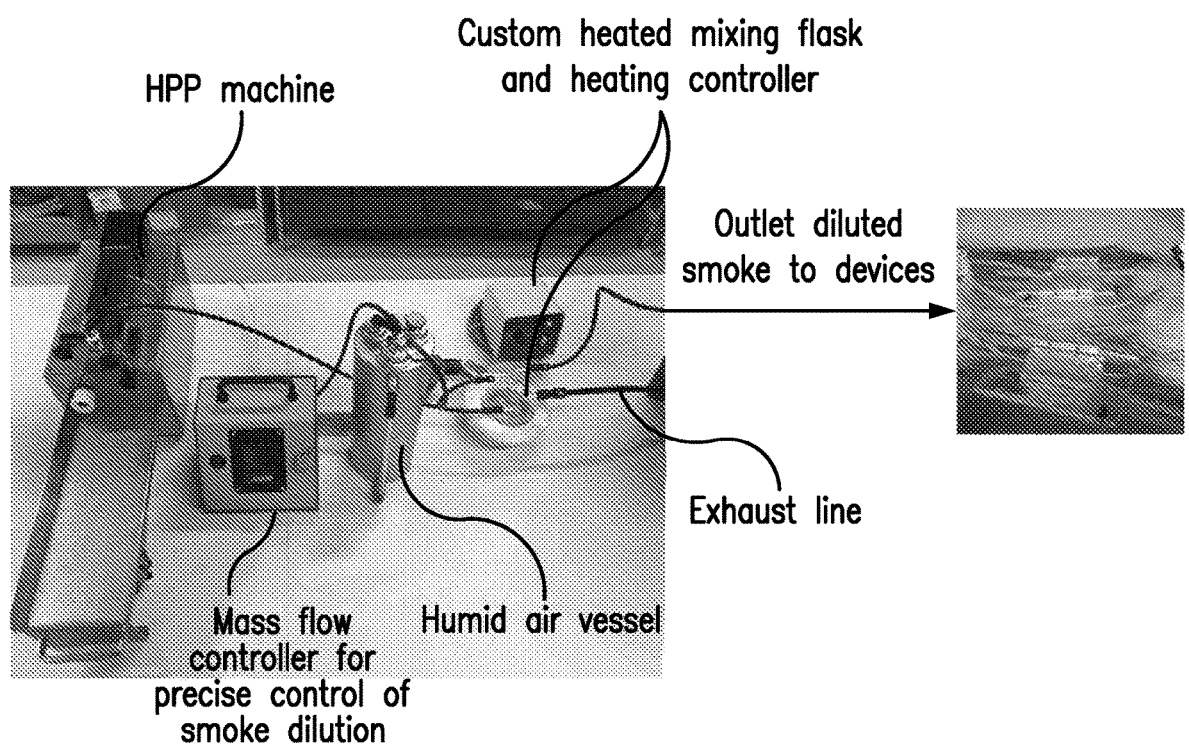
FIG. 8 depicts a microengineered biomimetic lung model according to certain embodiments depicting an exemplary method for delivering cigarette smoke.

In certain embodiments, the device delivers the agent to the first microchannel (e.g. FIG. 7). In certain embodiments, the device delivering the agent can be an automated machine (e.g. FIG. 8). In certain embodiments, the agent can be delivered to the first microchannel. In certain embodiments, the agent can be more dilute the deeper it moves into the microchannel. In certain embodiments, the agent can be delivered at the concentration and intermittent schedule as encountered by a human lung. In certain embodiments, the device can device can deliver the agent to the microchannel (s) through a port (e.g., FIGS. 1 and 2 (15)) in the body, wherein the first opening of the port 15 can be to the outside of the body and the second opening of the port 15 can be to at least one microchannel.

In certain embodiments, the device delivers smoke (e.g., cigarette smoke) to the first microchannel. In certain embodiments, the device delivers the smoke through the port 15 in the first outer body portion 13. In certain embodiments, when the smoke is delivered to the port 15 in the first outer body portion 13 it is delivered to only the first microchannel. In certain embodiments, the device delivering the smoke can be an automatic smoking machine (e.g. FIG. 8). For example, but not limited to, the automatic machine could be a benchtop-sized, automated smoking machine interfaced with microfluidic devices (e.g., a Human Puff Profile model cigarette smoking machine (CH Technologies)). In certain embodiments, the cigarette smoke can be delivered to the first microchannel such that the distribution of cigarette smoke mimics cigarette smoke exposure conditions experience by the cell lining in the human lung. In certain embodiments, the cigarette smoke can be more dilute the deeper it moves through the first microchannel. In certain embodiments, the Weibel model can be used to deliver the smoke. In certain embodiments, the smoke can be intermittently delivered to model the frequency in which a smoker's lungs may experience the smoke (e.g., to model a heavy versus light smoker). In certain embodiments, the concentration of the smoke mimics that of a lung exposed to secondhand smoke.

In certain embodiments, the device can be a model for fibrosis. In certain embodiments, the fibrosis model entails measuring fibroblast proliferation, fibroblast ECM production, and/or stiffening of the gel and/or tissue.

In certain embodiments, the biomimetic lung model can include additional elements, for example but not limited to, integrated pumps, valves, bubble traps, oxygenators, gas-exchangers, in-line microanalytical functions, and other suitable elements. Such elements can allow for additional control and experimentation using the biomimetic lung model. In certain embodiments, the biomimetic lung model can include features for automatically performing experiments on the biomimetic lung model. For example, in some embodiment, the biomimetic lung model can include automated valve or fluid (e.g., liquid or air) control mechanisms or automatic testing mechanisms, such as sensors or monitors. In certain embodiments, the biomimetic lung model can be configured to be coupled with other sensors or monitors not disclosed on the biomimetic lung model. In certain embodiments, the biomimetic lung model can include a cleaning reservoir coupled to the channels for cleaning or sterilizing the channels. In certain embodiments, the biomimetic lung model can be modular in construction, thereby allowing various elements to be attached or unattached as necessary during various cleaning, experimenting, and imaging processes. In certain embodiments, the biomimetic lung model, or portions thereof, can be reusable, and in some embodiments, the biomimetic lung model, or portions thereof, can be disposable.

In certain embodiments, the biomimetic lung model compositions disclosed herein can be used to study exchange of various endogenous and exogenous substances such as oxygen, nutrients, metabolic waste, and xenobiotics. Furthermore, in certain embodiments, the biomimetic lung model disclosed herein can provide opportunities to develop specialized human disease models that can use patient-derived cells to simulate complex human-specific disease processes for a variety of biomedical, pharmaceutical, toxicological, and environmental applications. For example, in certain embodiments, the biomimetic lung model disclosed herein can be used to study pulmonary pathologies as well as other pathophysiologic processes that can occur in the lung. Additionally, in certain embodiments, the biomimetic lung model compositions disclosed herein can be used as a screening tool to evaluate the safety and toxicity of environmental exposures (e.g., chemicals, toxins) and drugs, and the drug transfer between lung and surrounding tissue.

Cell Culture

In certain embodiments, the layer of cells 30 can be obtained from lung tissue. In certain embodiments, the layer of cells 30 can be obtained from a primary culture generated from lung tissue. Standard techniques of tissue harvesting and preparation can be used.

In certain embodiments, the layer of cells 30 can be an immortalized cell line.

In certain embodiments, adhering the layer of cells to the first side of the membrane can include standard approaches of extracellular matrix coating of the membrane, for example, but not limited to the use of fibronectin, prior to seeding of cells. In certain embodiments, to seed the cells, a high density cell suspension can be introduced to the channel and allowed to incubate under static conditions to allow the cells to adhere. In certain embodiments, the cell suspension is allowed to incubate for 2 to 4 hours. In certain embodiments, after the period of attachment flow can be initiated to allow the washing away of unattached cells and beginning the perfused culture stage. In certain embodiments, some cell proliferation can occur to fill out the entire membrane surface. In certain embodiments, cell proliferation is allowed to occur for 2-3 days.

In certain embodiments, the immune cells are obtained from peripheral blood and incorporated into the lung model. For example, peripheral blood monocytes can be obtained to generate the macrophage cells used in the model. In certain embodiments, THP-1 cells are used. In certain embodiments, macrophages can be obtained from patient biopsies and bronchoalveolar lavages.

In certain embodiments, the maccrophagees can be introduced into the channel after the epithelial layer has formed. For example, this can be accomplished by pipetting them into the channel. As they differentiate they adhere to the epithelial cells and crawl around. One way to test to see if they adhered is to wash the channel and check to see if they have not washed away.

In certain embodiments, the stromal cells are derived from a primary cell culture, established cell culture, or an immortalized cell culture. In certain embodiments, the stromal cells are obtained from a biopsied tissue.

In certain embodiments, the gel later contains nutrients to feed the cells. In certain embodiments, the cells in the gel layer obtain nutrients from culture medium from the microchannel or reservoir. In certain embodiments, the cells obtain nutrients from within the gel and/or from culture medium from the microchannel or reservoir.

The following examples are offered to more fully illustrate the invention, but are not to be construed as limiting the scope thereof.

EXAMPLES

Example 1: Smoking-Induced Disease Model of a Human Small Airway

Figure 9:
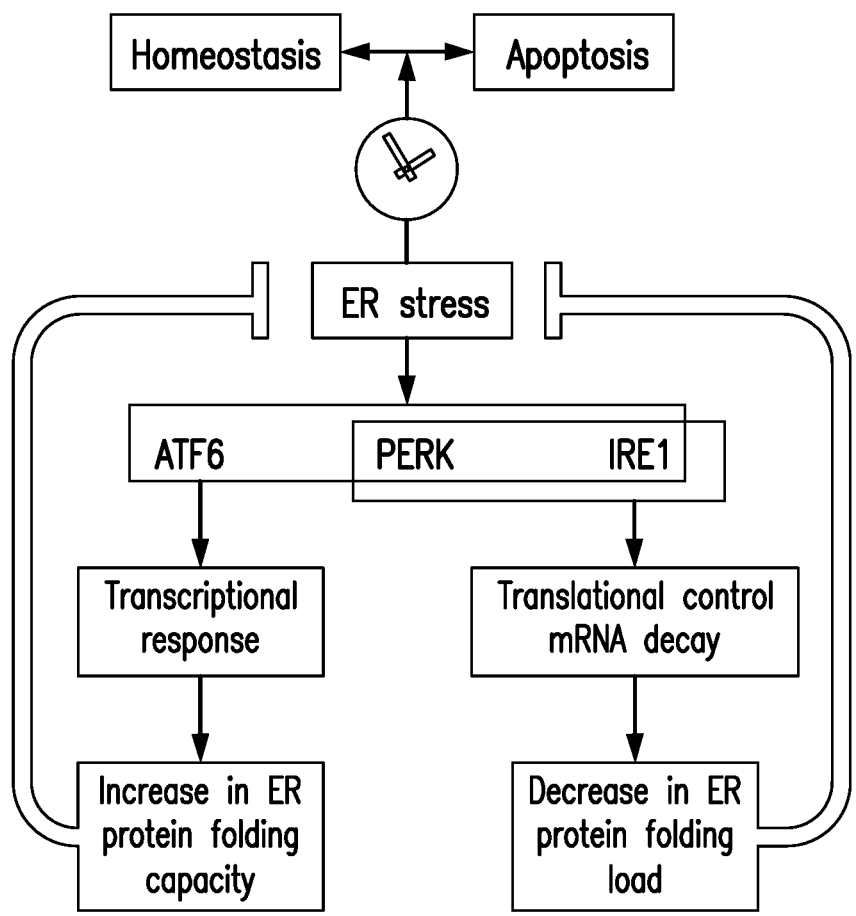
FIG. 9 depicts a schematic of UPR stress response.

Cigarette smoking-induced pathology involves induction of cellular stress responses in the epithelial cells lining the airways of human lungs, including activation of endoplasmic reticulum (ER) stress responses which result from the cell's inability to cope with its protein production demands. Acute smoke exposure causes oxidative stress, a consequence of which is disrupted proteostasis. As an example of one such response that can be probed in the biomimetic model, cells have evolved various mechanisms for coping with disrupted proteostasis, one of which is the Unfolded Protein Response (UPR) (FIG. 9). Stress tolerance leads to the return to homeostasis (proteostasis). Failure to restore homeostasis prompts a cell death program. Typically the apoptosis is immunologically silent; however, during heavy stress proinflammatory necrosis is prevalent. Thus, the cells either recover, or they don't and die, which is part of the beginning of the disease process that leads to COPD, fibrosis or other lung diseases. Any other disease relevant signaling pathway or cellular response mechanism can be assayed using standard cell biological methods in addition to the UPR, including but not limited to oxidative stress responses involving expression of Nrf-2 and inflammatory responses involving activation of NFkB coupled with the production and release of inflammation-modulating cytokines and chemokines.

It has been shown that the UPR is activated in the lungs of smokers with COPD (Jorgensen et al., 2008; Kelsen et al., 2008) and in the lungs of laboratory animals after exposure to the smoke of a single cigarette (Kenche et al., 2013), demonstrating the sensitivity of measuring UPR activation as an early injury response to smoke exposure.

The body of the model was formed using soft lithography techniques, in which the PDMS mixture was pour over the mold, and the body was allowed to cure. The microchannels were etched into the body, with the dimensions of 10 mm×1 mm×0.15 mm (length×width×height).

In this example, non-diseased small airway epithelial cells derived from healthy human donors (from Lonza) were used. Although Matrigel was applied to the membrane prior to seeding of the cells, any ECM coating (e.g. Fibronectin) can be used to enhance initial cell adhesion. A cell suspension in the range of 2-8 million cells/ml was introduced to the channel and allowed to incubate under static conditions for 2-4 hours. After the period of attachment, flow was initiated to wash away unattached cells. After cell proliferation was allowed to occur for 1-3 days, the medium was removed to initiate air-liquid interface culture. The length of submerged culture varies depending on the density of initial seeding.

Figure 10:
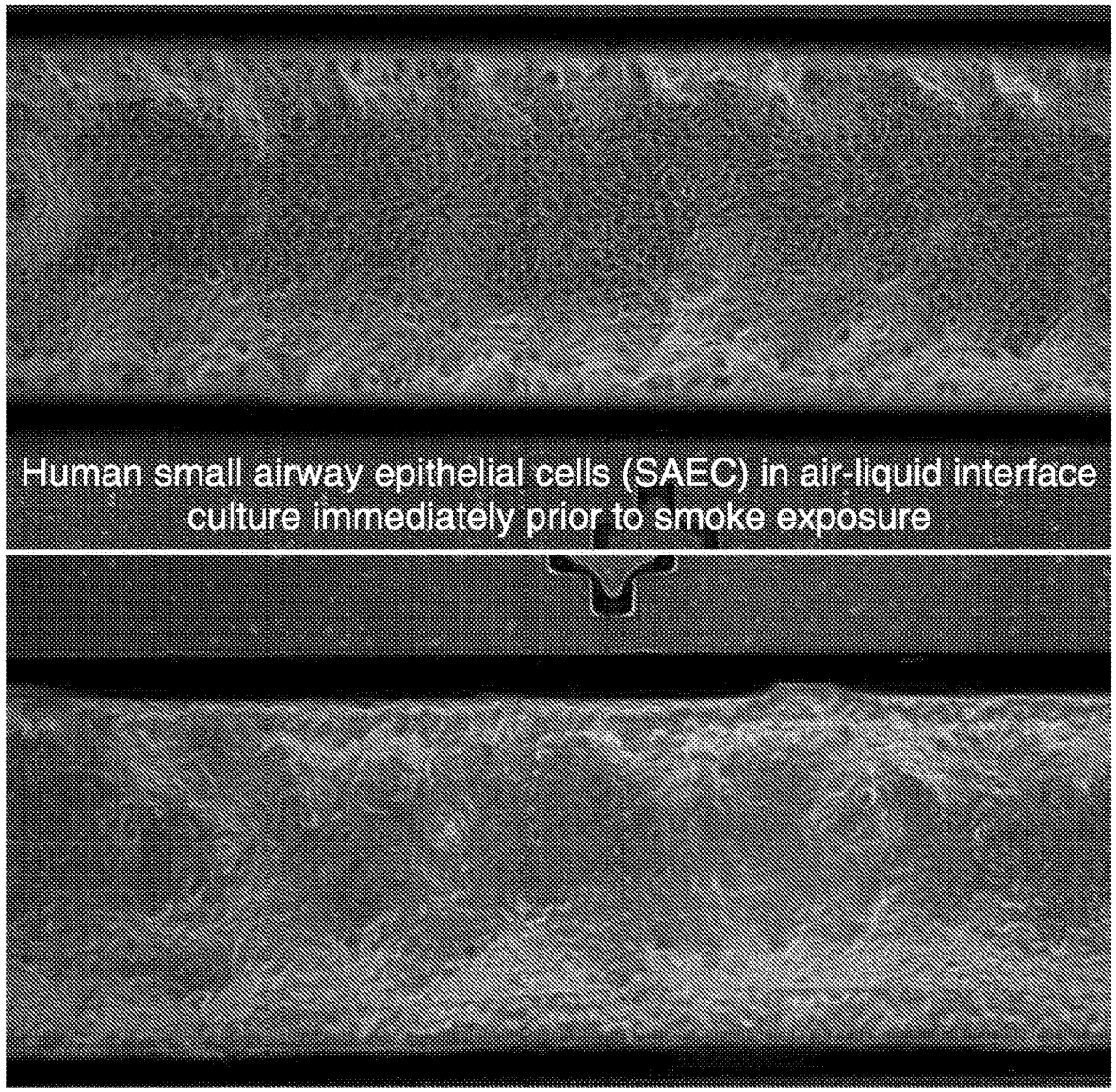
FIG. 10 depicts the cellular physiology of the biomimetic model before the exposure to an agent.

The device delivering the cell culture medium to the microchannels was disconnected from the body of the model before smoke was delivered to the microchannel above the membrane. Cell culture media remained in the lower microchannel to nourish the cells. A picture of the membrane populated by human small airway epithelial cells in air-liquid interface culture is shown in FIG. 10.

A lit cigarette was placed into a chamber to allow the smoke to accumulate. The air with smoke was channeled over the cells by pulling the smoke from the chamber through the upper microchannel of the model via a syringe device attached to the body of the model via a connecting tube.

UPR activation was measured by examining small airway epithelial expression of ATF6 and the phosphorylated form of EIF2a via immunohistochemistry and fluorescence microscopy.

Figure 11:
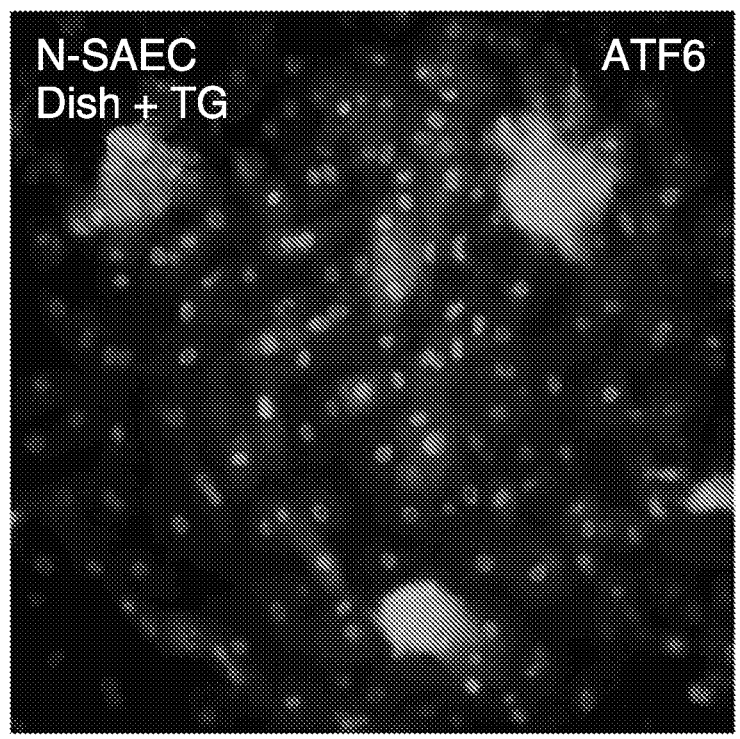
FIG. 11 depicts UPR induction via the staining of AFT6.
Figure 12:
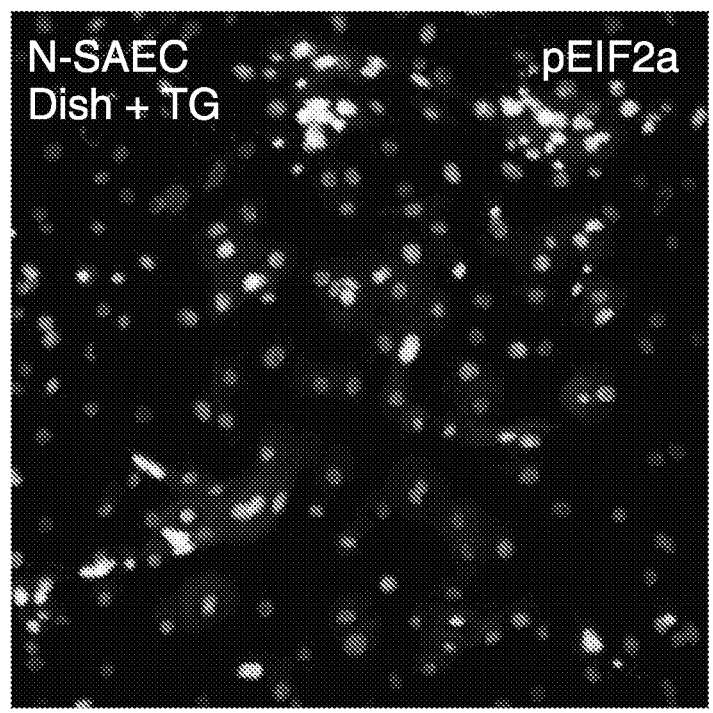
FIG. 12 depicts UPR induction via the staining of phosphorylated EIF2a (pEIF2a).
Figure 13A:
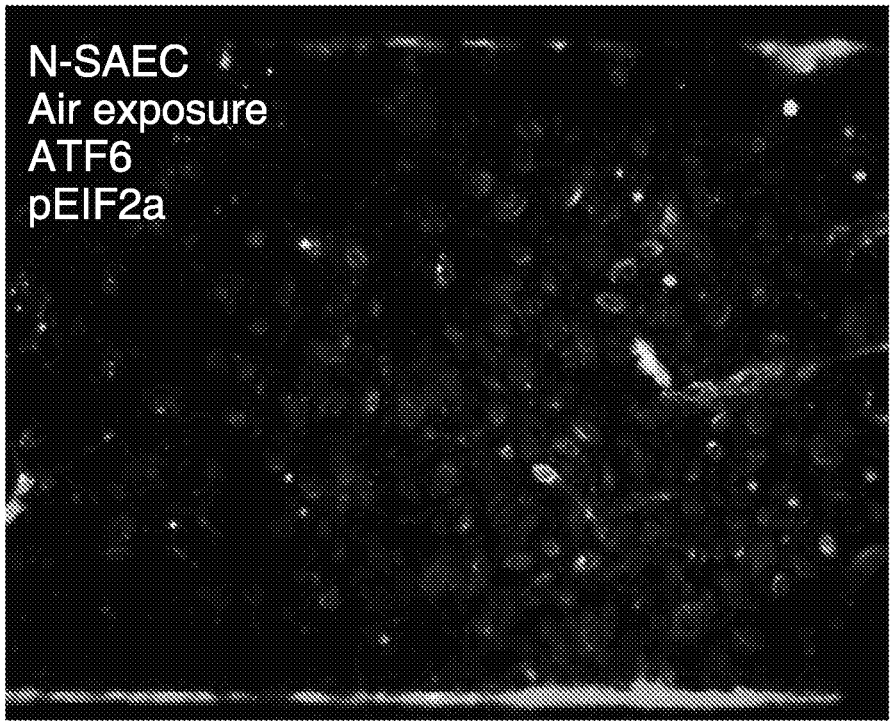
FIG. 13A-B. depicts UPR induction via staining of AFT6 and pEIF2a in (A) control/air treated cells and (B) smoke exposed cells.
Figure 13B:
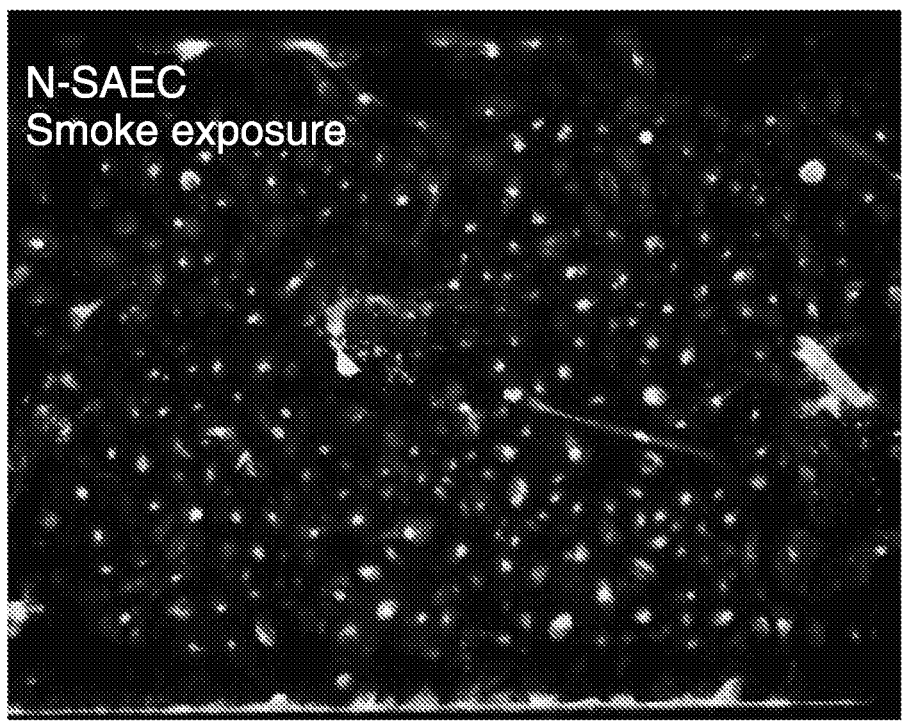

Up-regulation and nuclear translocation of ATF6 was observed (FIG. 11). Phosphorylation of EIF2a was also observed (FIG. 12) following exposure to highly diluted smoke of a single cigarette for approximately 2-3 minutes, demonstrating a highly sensitive cellular readout of early injury in response to smoke exposure.

Figure 14A:
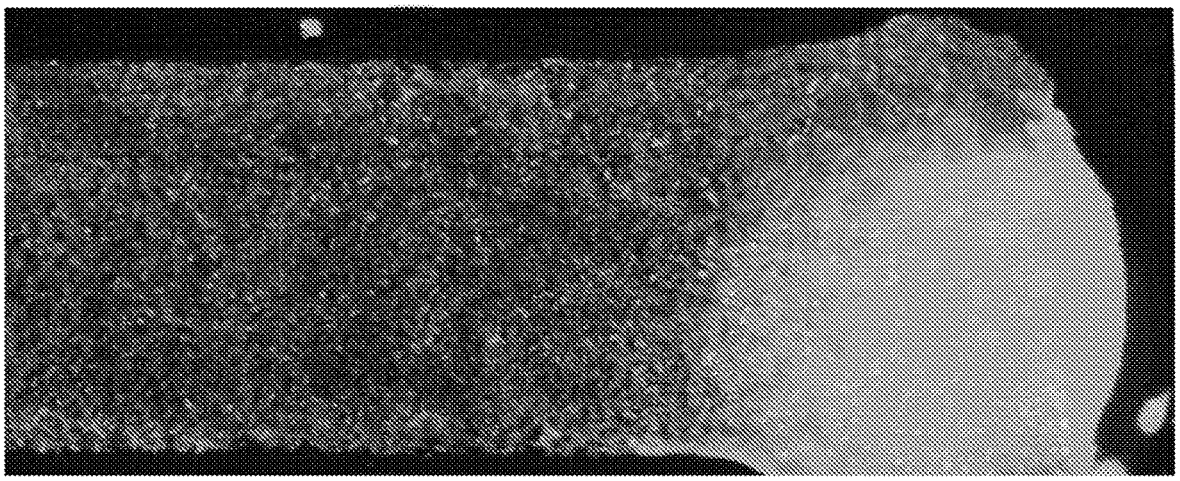
FIG. 14A-B. depicts cellular injury via staining of viable cells with calcein AM (green) and labeling of dead/dying cells with ethidium bromide (red) in (A) cells exposed to smoke for 4 hours and (B) cells exposed to air for 4 hours.
Figure 14B:
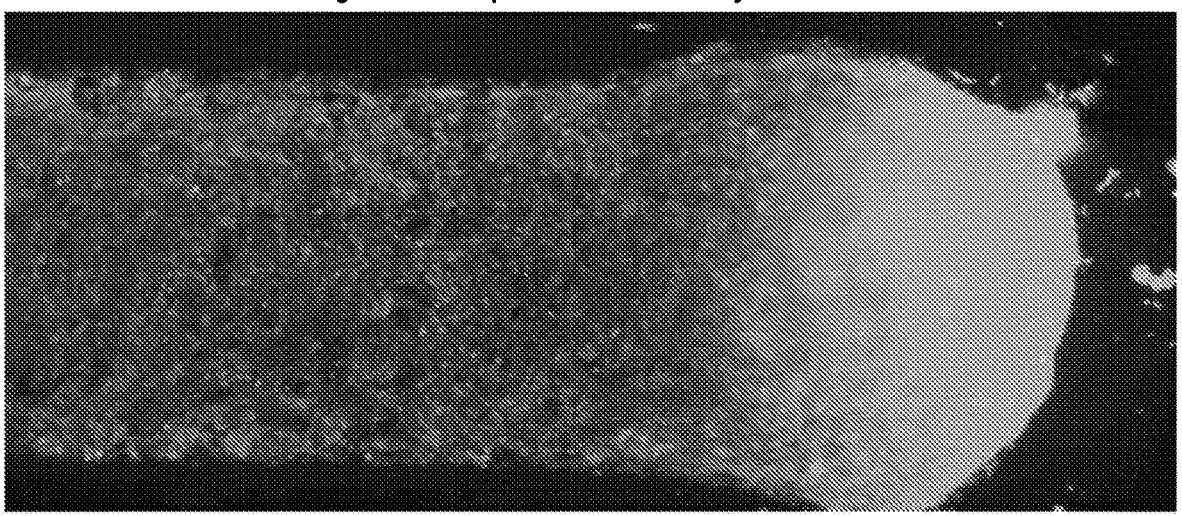

Even after exposure to small amounts of cigarette smoke (fractions of individual puffs), an increase in UPR protein staining (AFT6 green, pEIF2a red) was induced (FIG. 14B).

After 4 hours of smoke exposure at a dilution ration of 1-10% an increase in cellular injury was observed (FIG. 14A) as compared to cells exposed only to air (FIG. 14B).

Figure 15:
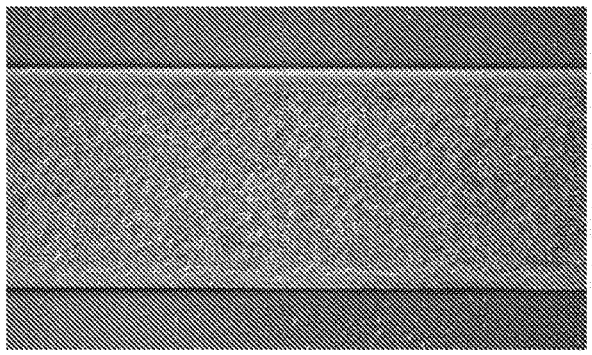
FIG. 15. depicts cell morphology in cells exposed to either air or smoke for 12 hours.
Figure 15:
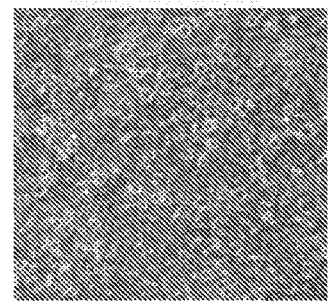
Figure 15:
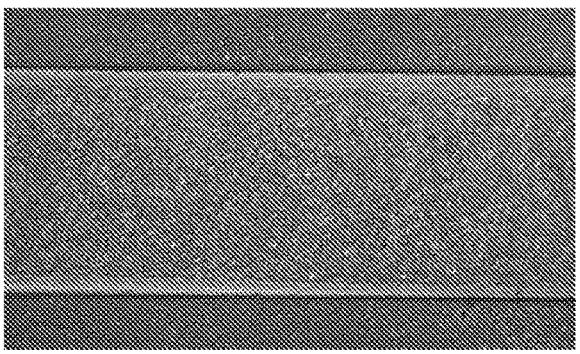
Figure 15:
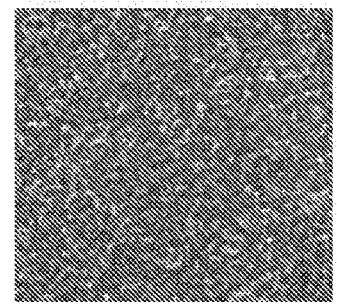

After 12 hours of smoke exposure at a dilution ration of 1-10% there was a dramatic change in the cellular morphology of the airway epithelial cells. In particular, a greater percentage of the cells were rounded, which indicated that the cells were likely dying by one of multiple mechanisms including necrosis or apoptosis (FIG. 15).

Figure 16A:
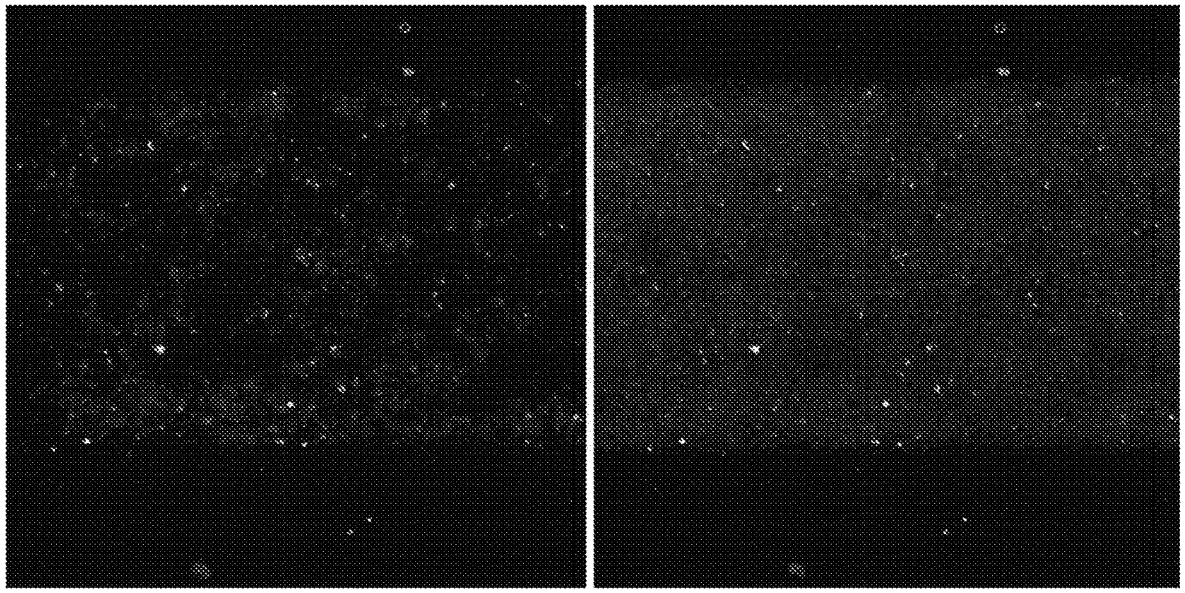
FIG. 16A-B. depicts UPR induction via staining of AFT6 and pEIF2a in (A) cells exposed to air for 16 hours and (B) cells exposed to smoke for 16 hours.
Figure 16B:
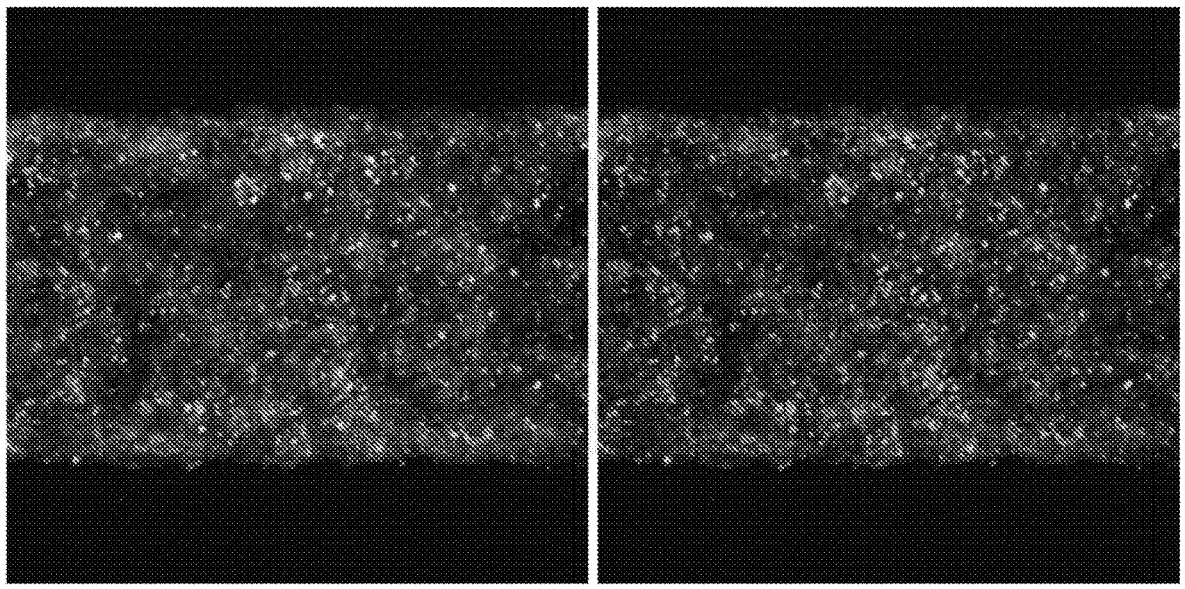

After 16 hours, very low levels of UPR activation (i.e., stress response) is seen in the control, air treated, cells (FIG. 16A). On the other hand, after 16 hours of exposure to smoke there was robust UPR activation in the exposed bronchial epithelial cells (FIG. 16B).

Single smoke exposure induced acute injury of human bronchial epithelial cells and small airway epithelial cells, leading to significant loss of epithelial integrity and barrier function. This injurious response was accompanied by increased stress in the endoplasmic reticulum, as manifested by robust activation of the unfolded protein response.

Figures 17A, 17B:
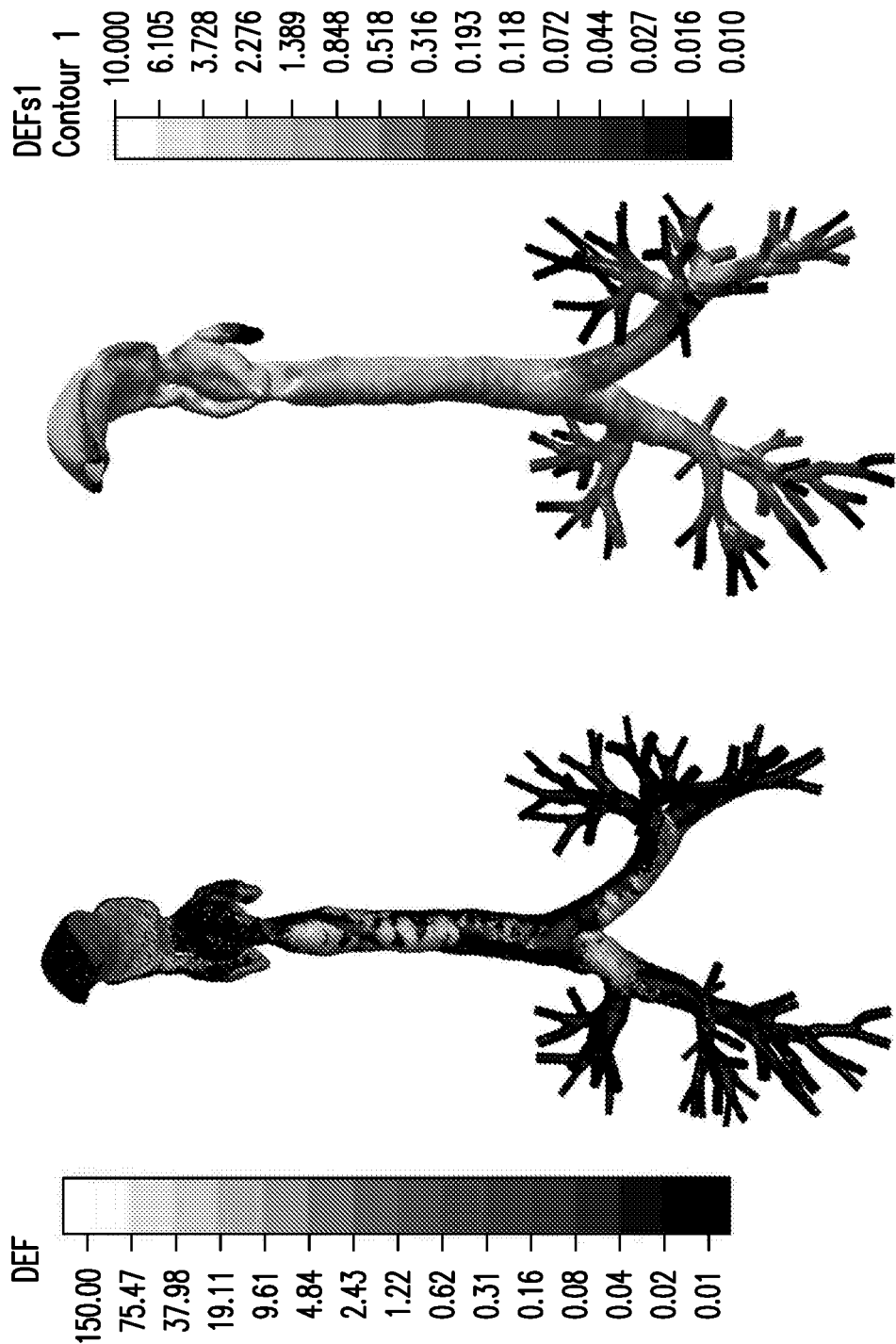
FIG. 17A-B depicts simulation data of lung models subject to cigarette smoke particles and vapor.

FIGS. 17A-B depict simulation data of lung models subject to cigarette smoke particles (FIG. 17A) and acrolein vapor (FIG. 17B). The disclosed simulation data indicates that dilutions of ~95% or greater are required to replicate the amounts of exposure expected at the depth of the small airways in a human smoker. These data in part informed the initial range of concentrations tested and the responses of cells in our biomimetic model corroborate these predictions. Particles less than 1% at entrance to small airways. Acrolein <4-5% at entrance to small airways.

Figure 18A:
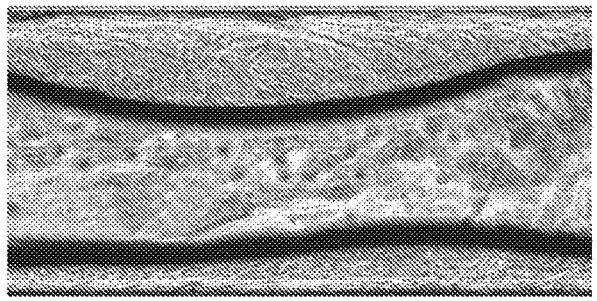
FIG. 18A-F depicts morphology and viability results of small airway epithelial cells exposed to smoke of a single cigarette
Figure 18B:
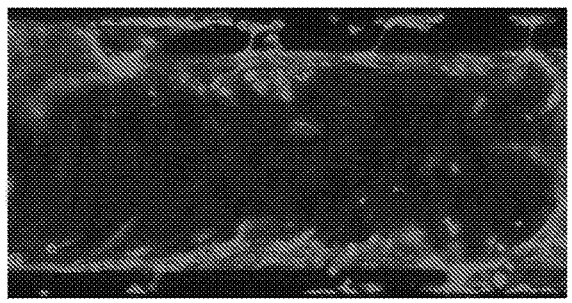
Figure 18C:
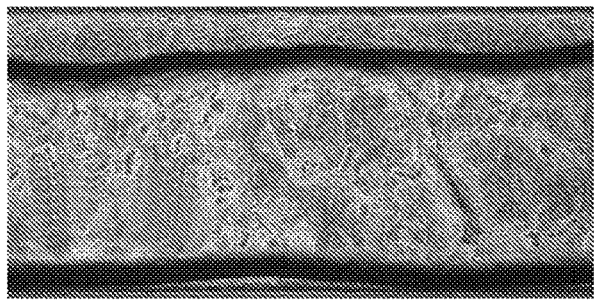
Figure 18D:
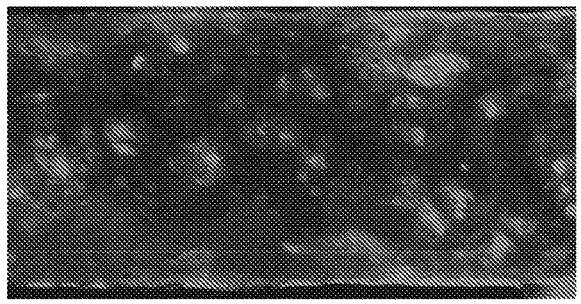
Figure 18E:
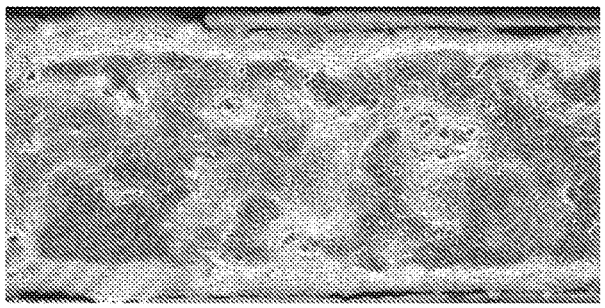
Figure 18F:
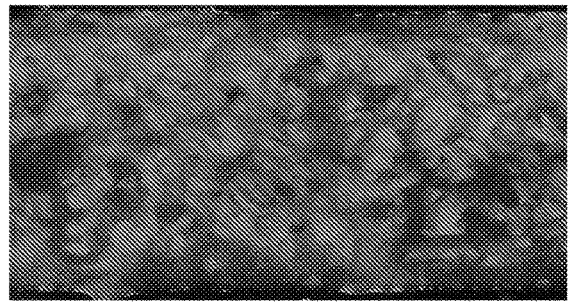

FIGS. 18A-F depict morphology and viability results of small airway epithelial cells exposed to smoke of a single cigarette. FIGS. 18A, 18C, and 18E depict morphology of small airway epithelial cells exposed to smoke of a single cigarette. FIGS. 18B, 18D, and 18F depict viability results of small airway epithelial cells exposed to smoke of a single cigarette corresponding to FIGS. 18A, 18C, and 18E, respectively. FIGS. 18A and 18B depict epithelial cells exposed to smoke of a single cigarette at 86% dilution. FIGS. 18C and 18D depict epithelial cells exposed to smoke of a single cigarette at 93% dilution. FIGS. 18E and 18F depict epithelial cells exposed to smoke of a single cigarette at 96.5% dilution under stable ALI post-exposure. As illustrated by FIGS. 18A-F, the integrity of the epithelial barrier maintained only at the high dilution of 96.5%. This is a requirement for performing multiple smoke exposures, and at the same time demonstrates the sensitivity of SAEC in the biomimetic model to small amounts of smoke. These results are on par with computer simulation predictions of expected smoke constituent concentrations at the level of the small airways as illustrated by FIG. 19.

Figure 19A:
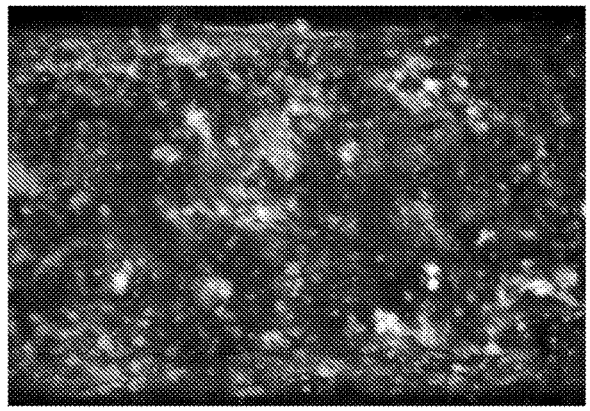
FIG. 19A-C depicts reduction of UPR activation following initial smoke exposure.
Figure 19B:
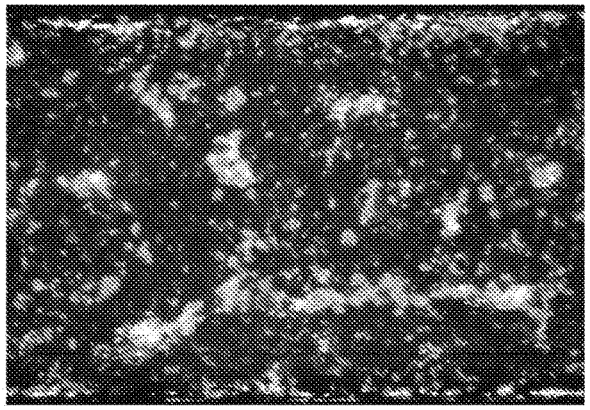
Figure 19C:
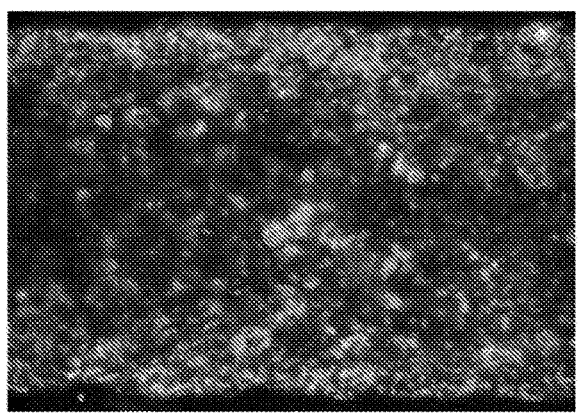

FIGS. 19A-C depict reduction of UPR activation following initial smoke exposure. FIGS. 19A, 19B, and 19C illustrate recovery and/or homeostasis results at 16 hours, 40 hours, and 64 hours, respectively. As illustrated by FIGS. 19A, 19B, and 19C, maintenance of the tissue layer integrity at low smoke dilution can allow for continuation of the experiments without channel filling to observe recovery of the cells from the initial injury. Additionally, maintenance of the tissue layer integrity at low smoke dilution can facilitate subsequent smoke exposures, such as the 8 day regimen used in the demonstrations of fibrotic response to smoke exposure of an incorporated stromal gel layer.

Example 2: COPD Disease Model

A biomimetic lung model was fabricated to mimic COPD in small airway cells. This model can be used to study modulation of the dysfunctional state in the epithelial cells, and to potentially discover/develop new therapeutics. Furthermore, outputs established using COPD-derived cells set a standard for establishing disease-relevant phenotypes in normal, healthy cells exposed to cigarette smoke as described in Example 1.

The body of the model was formed using soft lithography techniques, in which the PDMS mixture was pour over the mold, and the body was allowed to cure. The microchannels were etched into the body, with the dimensions of 10 mm×1 mm×0.15 mm (length×width×height).

Cells isolated from the lungs of smokers with COPD small airway cells were obtained from Lonza. A 2-8 million cells/ml density cell suspension was introduced to the channel and allowed to incubate under static conditions for 2-4 hours. After the period of attachment, flow was initiated to wash away unattached cells. After cell proliferation was allowed to occur for 1-3 days, the medium was removed to initiate air-liquid interface culture.

A lit cigarette was placed into a chamber to allow the smoke to accumulate. The air with smoke was channeled over the cells by pulling the smoke from the chamber through the upper microchannel of the model via a syringe device attached to the body of the model via a connecting tube.

Cells were stained for expression of ATF6 and pEIF2a, which are markers of the UPR response. They show high levels of activation in all conditions, which is indicative of their pathology. When smoked was delivered to the regular/normal airway cells, they started to express these same proteins found constitutively in the COPD cells (shown in Example 1).

Figure 20:
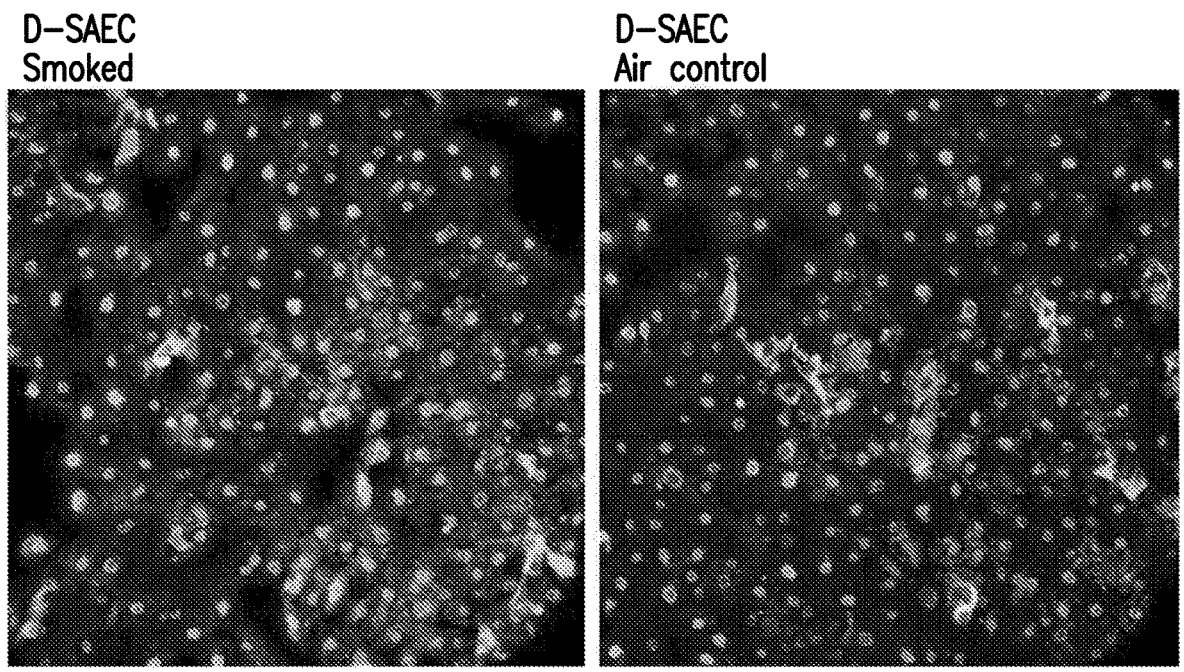
FIG. 20 depicts UPR induction via staining of AFT6 and pEIF2a in COPD cells exposed to smoke.

The cells were examined by immunohistochemistry and fluorescence microscopy. The similarity of the staining in both the control and the smoke exposed COPD cells demonstrated that the COPD cells have the disease characteristics regardless of in vitro smoke exposure (FIG. 20).

Figure 21:
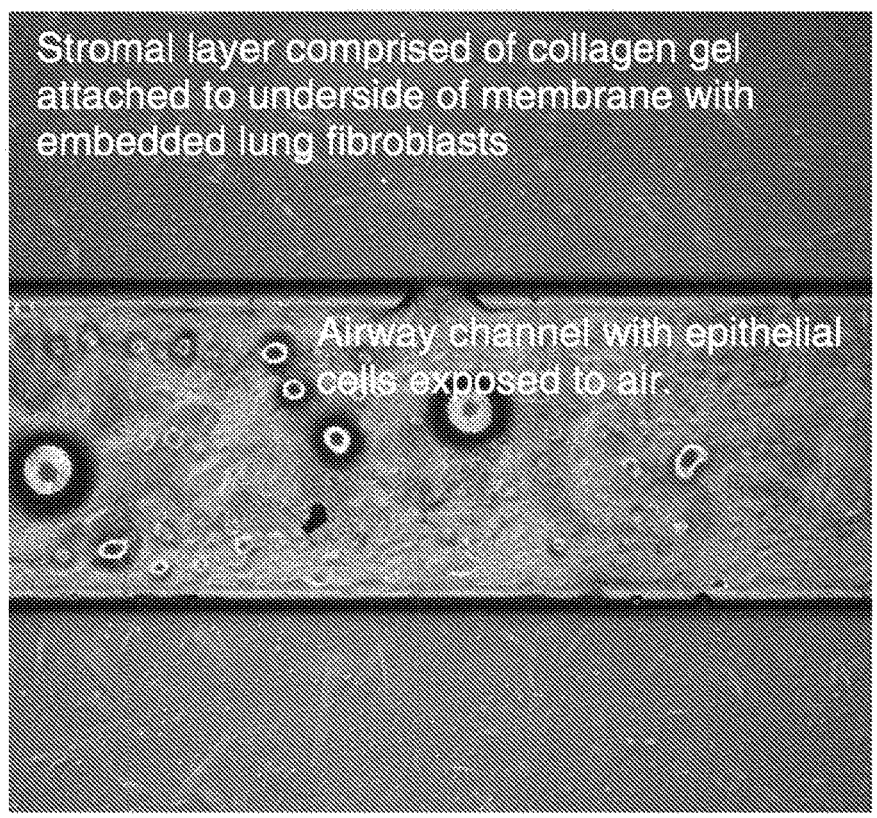
FIG. 21 depicts the cellular physiology of the biomimetic model according to certain embodiments, wherein the model incorporates the gel layer.

Example 3: Biomimetic Lung Model with Basal Stromal Tissue and Airway Lumen Macrophages A biomimetic lung model was fabricated to include both basal stromal tissue and airway lumen macrophages (FIG. 21).

The body of the model was formed using soft lithography techniques, in which the PDMS mixture was pour over the mold, and the body was allowed to cure. The microchannels were etched into the body, with the dimensions of 10 mm×1 mm×0.15 mm (length×width×height).

In this example, non-diseased small airway epithelial cells from healthy human donors (Lonza) were used. A 2-8 million cells/ml density cell suspension was introduced to the channel and allowed to incubate under static conditions for 2-4 hours. After the period of attachment, flow was initiated to wash away unattached cells. After cell proliferation was allowed to occur for 1-3 days, the medium was removed to initiate air-liquid interface culture.

The gel can be created by adding 1-8 mg of collagen to water, depending on the desired gel density and/or stiffness, and the liquid gel was kept at 4° C. In these examples, 2 mg/ml collagen gels were used. Instances when cells were added to the gel, they were added during this liquid phase. The membrane was treated with sulfo-sanpah to promote collagen/ECM anchorage. The gel was pipetted onto the underside of a membrane that had been stamped to the microchannel while the device was flipped upside down. Once the gel layer solidified by incubating at 37° C., the upper channel portion—now with a cast gel under the membrane—was flipped back over and placed over the reservoir layer to complete the device assembly.

Figure 22:
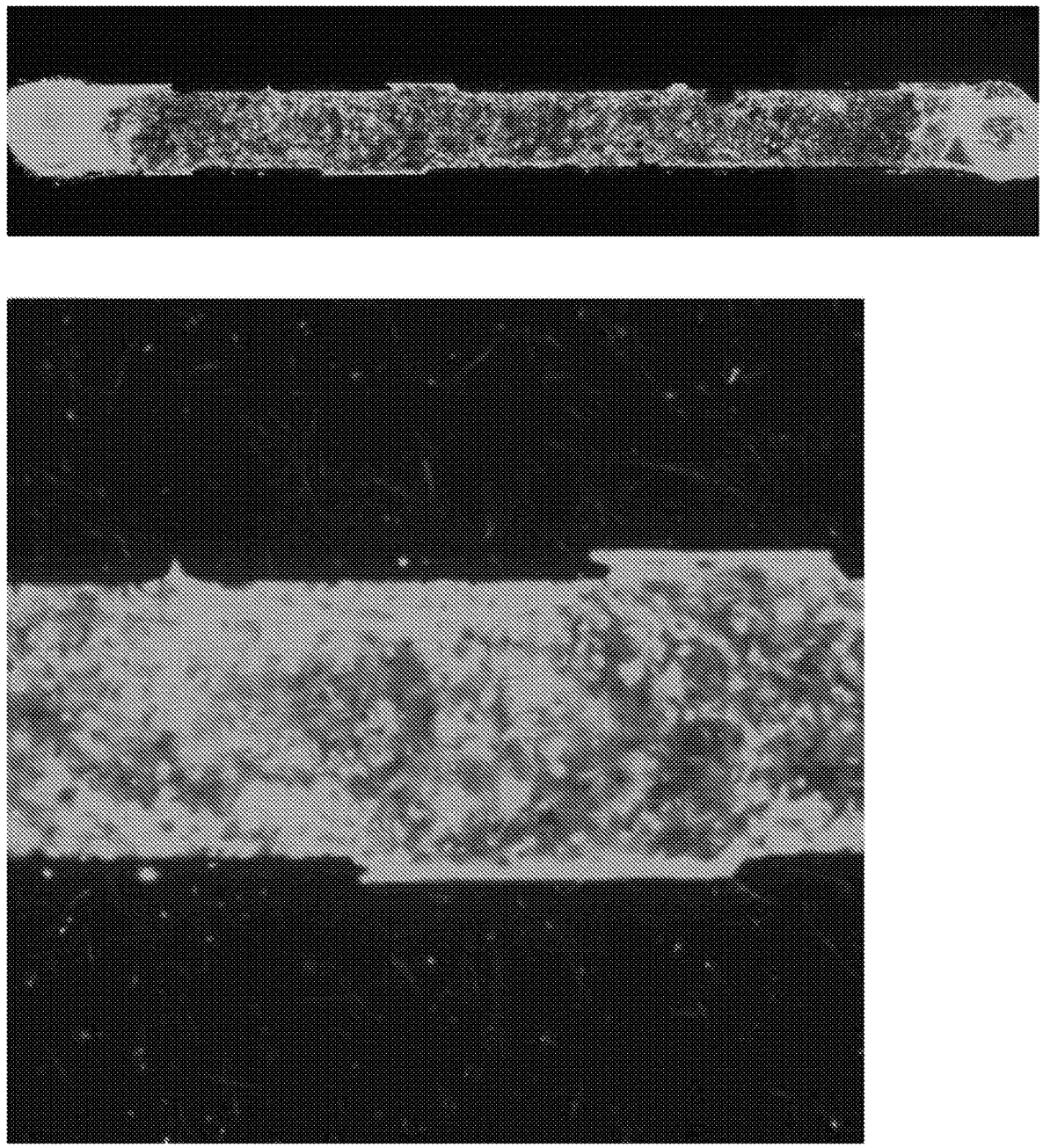
FIG. 22 depicts the cell viability of the biomimetic model after 72 hours of incorporating the gel layer.

The epithelial cells remained viable once the gel layer was attached to the underside of the membrane. In particular, FIG. 22 shows that after 72 hours after the attachment of the gel layer, the epithelial cells and stromal cells (fibroblasts) in the air-liquid interface configuration remained viable. Viability studies were conducted with an live/dead stain (calcein-AM and ethidium bromide) for simultaneous fluorescence staining of viable and dead cells.

Figure 23:
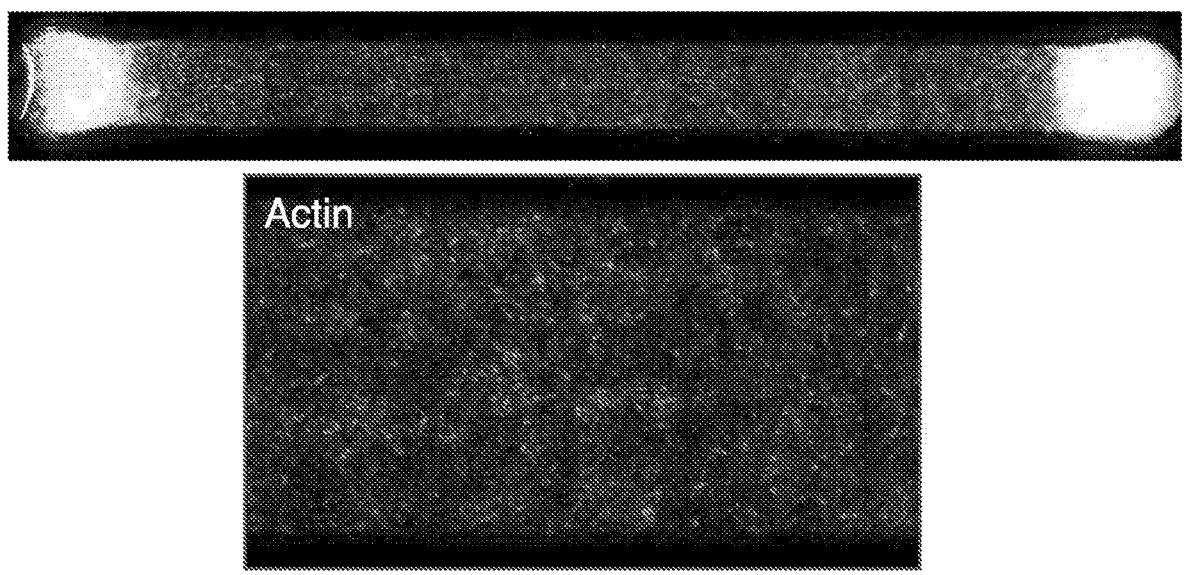
FIG. 23 depicts the incorporation of macrophages among the airway epithelial layer.

A THP-1 monocyte/macrophage cell line was also seeded onto the bronchial epithelial cell-lined channel. Staining with cell tracker die indicated that adherent/crawling macrophage-like cells were present on the surface of the airway epithelium, mimicking the multicellular complexity of the in vivo airway niche (FIG. 23).

Example 4: Fibrosis Disease Model

A biomimetic lung model is fabricated to mimic fibrosis in the small airway tissue niche of the human lung. This model can be used to study how modulation of the dysfunctional state in smoked epithelial cells can influence the fibroblasts and/or stromal cells in the adjacent gel layer of the biomimetic model, and to potentially discover/develop new therapeutics that inhibit pathological processes and promote tissue homeostasis.

In this model, the epithelial cells can be seeded onto the first side of the membrane within the upper microchannel. Fibroblasts are added to the gel layer prior to being cast and set upon the second side of the membrane as described above.

The present disclosure is well adapted to attain the ends and advantages mentioned as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified and all such variations are considered within the scope and spirit of the present disclosure. Various publications, patents and patent application are cited herein, the contents of which are hereby incorporated by reference in their entireties.

The invention claimed is:

1. A biomimetic lung model comprising:
a body having a first microchannel and a second microchannel disposed therein;
a membrane disposed between the first microchannel and the second microchannel, the membrane having a first side facing the first microchannel and a second side facing the second microchannel;
a layer of cells coating the first side of the membrane; and
tissue or cells embedded within a gel layer attached to the second side of the membrane, the embedded tissue or cells being in communication with the layer of cells on the first side of the membrane, wherein
at least one agent is delivered through at least one of the first microchannel and the second microchannel, and
the layer of cells comprises airway epithelial cells including one or more of nasal epithelial cells, tracheal epithelial cells, and small airway epithelial cells.

2. The biomimetic lung model of claim 1, wherein the membrane comprises one or more of polyester thin clear fabric, polydimethylsiloxane, polymeric compounds, and natural membranes.

3. The biomimetic lung model of claim 2, wherein the natural membranes comprising at least one of collagen and laminin.

4. The biomimetic lung model of claim 1, wherein the first microchannel has a width from about 0.5 mm to about 2 mm and a length from about 1000 µm to about 10 mm.

5. The biomimetic lung model of claim 4, wherein the first microchannel has a width from about 1 mm to about 2 mm and a length of about 1000 µm.

6. The biomimetic lung model of claim 1, wherein the layer of cells further comprises at least one type of macrophage cells, the at least one type of macrophage cells being one or more of alveolar, interstitial, intravascular, airway macrophages, and an immortalized macrophage cell line.

7. The biomimetic lung model of claim 1, wherein the at least one agent comprises one or more of cigarette smoke, nicotine aerosol, wood smoke, natural plant smoke, silica dust, acrylic dust, particulates, asbestos fibers, solvents, grain dust, bird droppings, and animal droppings.

8. The biomimetic lung model of claim 7, wherein the cigarette smoke is delivered to the first microchannel such that the distribution of cigarette smoke mimics cigarette smoke exposure conditions experienced by cell linings in the human lung.

9. The biomimetic lung model of claim 1, wherein the gel layer comprises extracellular matrix proteins, the extracellular matrix proteins being at least one of collagen, fibronectin, laminin, and hyaluronic acid.

10. The biomimetic lung model of claim 1, wherein the embedded tissue or cells comprise basal stromal tissue or cells.

11. The biomimetic lung model of claim 1, wherein the airway epithelial cells are obtained from a healthy human lung or a chronically diseased human lung.

12. The biomimetic lung model of claim 1, wherein the biomimetic lung model is configured to identify pharmaceutical compositions that alleviate a lung disease.

13. The biomimetic lung model of claim 1, wherein the biomimetic lung model is configured to identify agents harmful to the lung.

14. The biomimetic lung model of claim 1, wherein the at least one agent comprises cigarette smoke or nicotine aerosol, and the at least one agent is delivered to at least one of the first microchannel and the second microchannel of the biomimetic lung model at a dilution ratio of between about 1% agent and about 10% agent.

15. A method for fabricating a biomimetic lung disease model comprising:
(a) fabricating a body having a first microchannel and a second microchannel disposed thereon;
(b) inserting a membrane between the first microchannel and the second microchannel, the membrane having a first side facing the first microchannel and a second side facing the second microchannel;
(c) adhering airway epithelial cells on a surface of the first side of the membrane;
(d) casting a cell- or tissue-laden gel on a surface of the second side of the membrane, the gel being configured to solidify by incubation at body temperature; and
(e) delivering an agent to at least one of the first microchannel and the second microchannel, wherein
the agent is at least one of cigarette smoke, nicotine aerosol, wood smoke, natural plant smoke, silica dust, acrylic dust, particulates, asbestos fibers, solvents, grain dust, bird droppings, and animal droppings, and
the airway epithelial cells adhered on the surface of the first side of the membrane includes one or more of nasal epithelial cells, tracheal epithelial cells, and small airway epithelial cells.

16. The method of claim 15, wherein the adhering the airway epithelial cells comprises seeding a high density cell suspension upon the first side of the membrane and incubating the cell suspension for about 2 hours to about 4 hours.

17. The method of claim 15,
wherein the cell- or tissue-laden gel is laden with connective tissue.

18. The method of claim 15, wherein the cigarette smoke is delivered to the first microchannel and culture media is delivered to the second microchannel.

19. The method of claim 15, further comprising integrating macrophage cells among the airway epithelial cells.

* * * * *